US012807649B2

(12) United States Patent
Zhang et al.

(10) Patent No.: US 12,807,649 B2
(45) Date of Patent: Nov. 24, 2026

(54) CALCIUM INDEPENDENT PHOSPHATIDYLSERINE BINDING COMPOUNDS FOR DETECTING PHOSPHATIDYLSERINE POSITIVE CELLS

(71) Applicant: BIOLEGEND, INC., San Diego, CA (US)

(72) Inventors: Hong Zhang, San Diego, CA (US); Xinfang Zhao, San Diego, CA (US)

(73) Assignee: BIOLEGEND INC., San Diego, CA (US)

( * ) Notice: Subject to any disclaimer, the term of this patent is extended or adjusted under 35 U.S.C. 154(b) by 0 days.

(21) Appl. No.: 18/099,258

(22) Filed: Jan. 19, 2023

(65) Prior Publication Data

US 2024/0262865 A1 Aug. 8, 2024

(51) Int. Cl.
*C07K 7/64* (2006.01)
*G01N 33/58* (2006.01)

(52) U.S. Cl.
CPC ............ *C07K 7/64* (2013.01); *G01N 33/582* (2013.01); *C07K 2319/40* (2013.01)

(58) Field of Classification Search
None
See application file for complete search history.

(56) References Cited

U.S. PATENT DOCUMENTS 11,104,961 B2 8/2021 Fontanez et al.
2003/0138809 A1 7/2003 Williams
2020/0002716 A1 1/2020 Aponte et al.

FOREIGN PATENT DOCUMENTS

WO 2024155787 A2 7/2024

OTHER PUBLICATIONS

Cao et al. (Colloids and Surfaces A: Physicochemical and Engineering Aspects 626 (2021) 127026) (Year: 2021).*
Barth et al. (Nat Commun. Aug. 12, 2020;11(1):4027) (Year: 2020).*
Spears et al., Cysteine protecting groups: applications in peptide and protein science. Chemical Society Reviews. 2021; Issue 19.
International Preliminary Report on Patentability received for PCT Application No. PCT/US2024/011973 mailed on Jul. 31, 2025, 9 pages.
International Search Report and Written Opinion received for PCT Application No. PCT/US2024/011973 mailed on Jan. 10, 2025, 12 pages.
Chen, et al., "Single-Cell RNA-Seq Technologies and Related Computational Data Analysis", Frontiers in Genetics, vol. 10, Article 317, Apr. 5, 2019, pp. 1-13.
Deleersnijder, et al., "Current Methodological Challenges of Single-Cell and Single-Nucleus RNA-Sequencing in Glomerular Diseases", Journal of the American Society of Nephrology, vol. 32, No. 8, Aug. 2021, pp. 1838-1852.
Eberwine, et al., "The Promise of Single-Cell Sequencing", Nature Methods, vol. 11, Jan. 2014, pp. 25-27.
El-Faham, et al., "COMU: A Safer and More Effective Replacement for Benzotriazole-Based Uronium Coupling Reagents", Chemistry, vol. 15, No. 37, 2009, pp. 9404-9416.
Engeland, et al., "Annexin V-Affinity Assay: A Review on an Apoptosis Detection System Based on Phosphatidylserine Exposure", Cytometry, vol. 31, 1998, pp. 1-9.
Gang, et al., "Cyclic Peptides: Promising Scaffolds for Biopharmaceuticals", Genes, vol. 9, No. 11: 557, Nov. 16, 2018, pp. 1-15.
Hill, et al., "Constraining Cyclic Peptides to Mimic Protein Structure Motifs", Angewandte Chemie (International ed. in English), vol. 53, No. 48, 2014, pp. 13020-13041.
Kay, et al., "Sensing Phosphatidylserine in Cellular Membranes", Sensors, vol. 11, No. 2, Jan. 28, 2011, pp. 1744-1755.
Klein, et al., "Droplet Barcoding for Single-Cell Transcriptomics Applied to Embryonic Stem Cells", Cell, vol. 161, No. 5, May 21, 2015, pp. P1187-P1201.
Koopman, et al., "Annexin V for Flow Cytometric Detection of Phosphatidylserine Expression on B Cells Undergoing Apoptosis", Blood, vol. 84, No. 5, Sep. 1, 1994, pp. 1415-1420.
Ma, et al., "Calcium-dependent and -independent Annexin V Binding: Distinct Molecular Behaviours at Cell Membrane Interfaces", Chemical Communications, vol. 56, No. 11, 2020, pp. 1653-1656.
Macosko, et al., "Highly Parallel Genome-wide Expression Profiling of Individual Cells Using Nanoliter Droplets", Cell, vol. 161, No. 5, May 21, 2015, pp. P1202-P1214.
Mendive-Tapia, et al., "Preparation of a Trp-BODIPY Fluorogenic Amino Acid to Label Peptides for Enhanced Live-cell Fluorescence Imaging", Nature Protocols, vol. 12, Jul. 13, 2017, pp. 1588-1619.
Mendive-Tapia, et al., "Spacer-free BODIPY Fluorogens in Antimicrobial Peptides for Direct Imaging of Fungal Infection in Human Tissue", Nature Communications, vol. 7, Article 10940, Mar. 9, 2016, pp. 1-9.
Olofsson, et al., "Tryptophan-BODIPY: A Versatile Donor-acceptor Pair for Probing Generic Changes of Intraprotein Distances", Physical Chemistry Chemical Physics, vol. 8, 2006, pp. 3130-3140.
Pennisi, "Chronicling Embryos, Cell by Cell, Gene by Gene", Science, vol. 360, No. 6387, 2018, p. 367.
Saliba, et al., "Single-cell RNA-seq: Advances and Future Challenges", Nucleic Acids Research, vol. 42, No. 14, Jul. 22, 2014, pp. 8845-8860.

(Continued)

*Primary Examiner* — Sergio Coffa
(74) *Attorney, Agent, or Firm* — LOZA & LOZA, LLP

(57) ABSTRACT

The present invention relates to the phosphatidylserine (PS) binding compound derivative and the fusion of PS binding compound with an arm compound. The present invention describes the methods of producing and using PS binding compound derivative and the fusion of PS binding compound with an arm compound by providing the functional group to couple with functional group containing fluorophore for multicolor flow cytometry and multiplex imaging; to conjugate with magnetic particle for depleting the PS positive cells; to couple with oligo comprising PCR handle sequence, and unique DNA barcode for PS positive cells and capture sequence for discriminating positive cells from live cells in Single-cell RNA sequencing.

17 Claims, 20 Drawing Sheets

Specification includes a Sequence Listing.

(56) References Cited

OTHER PUBLICATIONS

Schmitt, et al., "Synthesis of the Core Compound of the BODIPY Dye Class: 4,4'-Difluoro-4-bora-(3a,4a)-diaza-s-indacene", Journal of Fluorescence, vol. 19, 2009, pp. 755-758.
Spears, et al., "Cysteine Protecting Groups: applications in Peptide and Protein Science", Chemical Society Reviews, vol. 50, No. 19, 2021, pp. 11098-11155.
Stockert, et al., "Fluorescence Microscopy in Life Sciences", Bentham Science Publishers, 2017, pp. 61-95.
Subiros-Funosas, et al., "A Trp-BODIPY Cyclic Peptide for Fluorescence Labelling of Apoptotic Bodies", Chemical Communications, vol. 53, 2017, pp. 945-948.
Tram, et al., "The Synthesis and Crystal Structure of Unsubstituted 4,4-difluoro-4-bora-3a,4a-diaza-s-indacene (BODIPY)", Dyes and Pigments, vol. 82, No. 3, Sep. 2009, pp. 392-395.
Vermes, et al., "A Novel Assay for Apoptosis Flow Cytometric Detection of Phosphatidylserine Expression on Early Apoptotic Cells Using Fluorescein Labelled Annexin V", Journal of Immunological Methods, vol. 184, No. 1, Jul. 1995, pp. 39-51.
White, et al., "Discovery and Optimization of Peptide Macrocycles", Expert Opinion on Drug Discovery, vol. 11, No. 12, 2016, pp. 1151-1163.
Choi, et al., "Single-Cell RNA Sequencing and Its Combination with Protein and DNA Analyses", Cells, vol. 9, No. 5, Article 1130, May 4, 2020, 34 pages.
Der, et al., "Single-cell RNA sequencing for the study of lupus nephritis", Lupus Science & Medicine, vol. 6, No. 1, Article e000329, Jun. 2019, 8 pages.
Giedt, et al., "Single-cell barcode analysis provides a rapid readout of cellular signaling pathways in clinical specimens", Nature Communications, vol. 9, No. 1, Article 4550, Oct. 31, 2018, 10 pages.
Greenblatt, et al., "The Unmixing Problem: A Guide to Applying Single-Cell RNA Sequencing to Bone", Journal of Bone and Mineral Research, vol. 34, No. 7, Jul. 2019, pp. 1207-1219.
Griffiths, et al., "Detection and removal of barcode swapping in single-cell RNA-seq data", Nature Communications, vol. 9, Article 2667, Jul. 10, 2018, 6 pages.
Hughes, et al., "Highly Efficient, Massively-Parallel Single-Cell RNA-Seq Reveals Cellular States and Molecular Features of Human Skin Pathology", BioRxiv, Jul. 2, 2019, 51 pages.
Jin, et al., "Cross-amplified Barcodes on Slides for Spatial Transcriptomics Sequencing", BioRxiv, 2022, 14 pages.
Masuyama, et al., "DNA barcodes evolve for high-resolution cell lineage tracing", Current Opinion in Chemical Biology, vol. 52, Oct. 2019, pp. 63-71.
Pai, et al., "High-throughput and single-cell T cell receptor sequencing technologies", Nature Methods, vol. 18, No. 8, Aug. 2, 2021, pp. 881-892.
Replogle, et al., "Combinatorial single-cell CRISPR screens by direct guide RNA capture and targeted sequencing", Nature biotechnology, vol. 38, No. 8, Aug. 2020, pp. 954-961.
Rosenberg, et al., "Scaling single cell transcriptomics through split pool barcoding", BioRxiv, Feb. 2, 2017, 13 pages.
Tambe, et al., "Barcode identification for single cell genomics", BMC Bioinformatics, vol. 20, Article 32, Jan. 17, 2019, 9 pages.
Zhang, et al., "Sample-multiplexing approaches for single-cell sequencing", Cellular and Molecular Life Sciences, vol. 79, Article 466, Aug. 5, 2022, 23 pages.
Zilionis, et al., "Single-cell barcoding and sequencing using droplet microfluidics", Nature Protocols, vol. 12, No. 1, Jan. 2017, pp. 44-73.

* cited by examiner

Cyclic Item-3

```
                                    SEQUENCE LISTING


Sequence total quantity: 11
SEQ ID NO: 1            moltype = AA  length = 7
FEATURE                 Location/Qualifiers
source                  1..7
                        mol_type = protein
                        organism = synthetic construct
SITE                    6
                        note = W=W(BODIPY). W(BODIPY) is Fmoc-labelled amino acid
                         of Trp attached to a BODIPY
                         (4,4-difluoro-4-bora-3a,4a-diaza-s-indacene) dye through a
                         spacer-free C-C linkage.
SEQUENCE: 1
RKKWFWG                                                                    7

SEQ ID NO: 2            moltype = AA  length = 7
FEATURE                 Location/Qualifiers
source                  1..7
                        mol_type = protein
                        organism = synthetic construct
SEQUENCE: 2
RKKWFWC                                                                    7

SEQ ID NO: 3            moltype = AA  length = 7
FEATURE                 Location/Qualifiers
source                  1..7
                        mol_type = protein
                        organism = synthetic construct
SITE                    7
                        note =
                         G=propargylglycine=Fmoc-Propargyl-Gly-OH=Fmoc-Pra-OH=Pra.
                         Pra is Fmoc protected Glycine  derivative.  It is a
                         synthsized unnature amino acid not only containing one
                         amine group and one carboxyl group but also containing one
                         alykene funcational group.  Pra is  commercial available.
REGION                  1..7
                        note = The amine and carboxyl groups are utilized to
                         facilitate head-to-tail cyclization of amino acids located
                         at positions 1..7 within the cyclic peptide. The alkyne
                         group serves as a key functional group for alkyne-azide
                         reactions.
SEQUENCE: 3
RKKWFWG                                                                    7

SEQ ID NO: 4            moltype =   length =
SEQUENCE: 4
000

SEQ ID NO: 5            moltype = AA  length = 7
FEATURE                 Location/Qualifiers
source                  1..7
                        mol_type = protein
                        organism = synthetic construct
SITE                    7
                        note =
                         G=propargylglycine=Fmoc-Propargyl-Gly-OH=Fmoc-Pra-OH=Pra.
                         Pra is Fmoc protected Glycine  derivative.  It is a
                         synthsized unnature amino acid not only containing one
                         amine group and one carboxyl group but also containing one
                         alykene funcational group.  Pra is  commercial available.
VARIANT                 7
```

```
                        note = Pra contains alkyne functional group, which links
                         with azide functional group containing "Arm". Arm=
                         Xa1(azido)-Xa2-(pol-Xa3)m. Xa1=azido-Lysine or
                         azido-propargylglycine or azido-L-propargylglycine or
                         azido-histidine or azido-tryptophan or azido-phenylalanine
                         orazido-arginine or azido-glutamine orazido-glycine or
                         azido-valine or azido-alanine. Azide group links with
                         alykene group in Pra. Xa2=Lys or  Arg or His or Ser or Thr
                         or Cys or  Asn or Gln or Pra or Tyr. (pol-Xa3)m, wherein
                         pol=polymer wherein m= 1 to 10, wherein polymer=(PEG)n, or
                         (PEG)n or (PEO)n or (Epsilon-Caprolactam)n or (CH2)n or
                         [(PEG)n(CH2)n] wherein n=1 to 60, preferably 1 to 24, more
                         preferablely 1 to 12. PEG=Fmoc-NH-PEG-COOH. Xa3=Lys or Arg
                         or His or Met or Cys or Pra
REGION                  1..7
                        note = The amine and carboxyl groups are utilized to
                         facilitate head-to-tail cyclization of amino acids located
                         at positions 1..7 within the cyclic peptide. The alkyne
                         group serves as a key functional group for alkyne-azide
                         reactions.
SEQUENCE: 5
RKKWFWG                                                                 7

SEQ ID NO: 6            moltype =   length =
SEQUENCE: 6
000

SEQ ID NO: 7            moltype = AA  length = 7
FEATURE                 Location/Qualifiers
source                  1..7
                        mol_type = protein
                        organism = synthetic construct
SITE                    7
                        note =
                         G=propargylglycine=Fmoc-Propargyl-Gly-OH=Fmoc-Pra-OH=Pra.
                         Pra is Fmoc protected Glycine  derivative.  It is a
                         synthsized unnature amino acid not only containing one
                         amine group and one carboxyl group but also containing one
                         alykene funcational group.  Pra is  commercial available.
REGION                  1..7
                        note = The amine and carboxyl groups are utilized to
                         facilitate head-to-tail cyclization of amino acids located
                         at positions 1..7 within the cyclic peptide. The alkyne
                         group serves as a key functional group for alkyne-azide
                         reactions.
VARIANT                 7
                        note = Pra contains alkyne functional group, which links
                         with azide functional group containing "Arm".
                         Arm=Xa1-Xa2-Pol-Xa3.  Xa1=azido-Lysine or
                         azido-propargylglycine or azido-L-propargylglycine or
                         azido-histidine or azido-tryptophan or azido-phenylalanine
                         or azido-arginine or azido-glutamine or azido-glycine or
                         azido-valine or azido-alanine. Azide group links with
                         alykene group in Pra. Xa2=Lys or Arg or  His or Ser  or
                         Thr or Cys or Asn or Gln or Pra or Tyr. Pol=Polymer=(PEG)n
                         or (PEO)n or  (Epsilon-Caprolactam)n or (CH2)n or
                         [(PEG)n(CH2)n], wherein n=1 to 60, preferably 1 to 24,
                         more preferably 1 to 12. PEG=Fmoc-NH-PEG-COOH. Xa3=Cys or
                         Pra or Met or Lys or Arg or His
SEQUENCE: 7
RKKWFWG                                                                 7

SEQ ID NO: 8            moltype = DNA  length = 69
FEATURE                 Location/Qualifiers
source                  1..69
                        mol_type = other DNA
                        organism = synthetic construct
modified_base           67^68
                        mod_base = OTHER
                        note = ^=a phosphorothioated bond
modified_base           68^69
                        mod_base = OTHER
                        note = ^=a phosphorothioated bond
SEQUENCE: 8
ccttggcacc cgagaattcc aatcgtcgag agctagbaaa aaaaaaaaaa aaaaaaaaaa  60
aaaaaaaaa                                                          69

SEQ ID NO: 9            moltype = DNA  length = 21
FEATURE                 Location/Qualifiers
```

-continued

```
source                  1..21
                        mol_type = other DNA
                        organism = synthetic construct
SEQUENCE: 9
ccttggcacc cgagaattcc a                                          21

SEQ ID NO: 10           moltype = DNA  length = 15
FEATURE                 Location/Qualifiers
source                  1..15
                        mol_type = other DNA
                        organism = synthetic construct
SEQUENCE: 10
atcgtcgaga gctag                                                 15

SEQ ID NO: 11           moltype = DNA  length = 30
FEATURE                 Location/Qualifiers
source                  1..30
                        mol_type = other DNA
                        organism = synthetic construct
SEQUENCE: 11
aaaaaaaaaa aaaaaaaaaa aaaaaaaaaa                                 30
```

CALCIUM INDEPENDENT PHOSPHATIDYLSERINE BINDING COMPOUNDS FOR DETECTING PHOSPHATIDYLSERINE POSITIVE CELLS

REFERENCE TO AN ELECTRONIC SEQUENCE LISTING

The contents of the electronic sequence listing (HZ_SEQ_Amended.xml; Size: 16,840 bytes; and Date of Creation: Apr. 2, 2023) is herein incorporated by reference in its entirety.

BACKGROUND OF THE INVENTION

Phosphatidylserine (PS), a phospholipid with a negatively charged head-group, is an essential component of bilayer cell membranes and is normally present in the inner leaflet. In the physiological state, PS exposure on external leaflet not only acts as an engulfment signal for phagocytosis apoptotic and dead cells but also participates in eliminating unwanted cells during early development and facilitating tumor growth and metastasis. In daily practice, PS positive dead cells can lead to false positive because they have greater autofluorescence and increase the non-speficity antibody binding, which can affect the quality of the data, especially in flow cytometry experiment. Thus, PS binding agent has been widely used as an important biomarker for detecting, monitoring and depleting PS positive cells from heterogenous cellular population.

Annexin V (or Annexin A5), a recombinant protein, is the most widely used PS binding agent specifically binding to PS in the presence of calcium (Vermes et al., *A novel assay for apoptosis Flow cytometric detection of phosphatidylserine expression on early apoptotic cells using fluorescein labelled Annexin V*. Journal of Immunological Methods. 1995; Volume 184, Issue 1, 17 July). In recent study, distinct annexin V binding behavior in $Ca^{2+}$-dependent and $Ca^{2+}$ independent cases were comparatively investigated using sum frequency generation vibrational spectroscopy (Ma et al., *Calcium-dependent and -independent annexin V binding: distinct molecular behaviours at cell membrane interfaces*. Chem Commun. 2020; February 6; 56(11):1653-1656). The paper data showed that the initial $Ca^{2+}$-independent binding went through a transition with annexin V reorientation to a more stable state upon adding $Ca^{2+}$. It demonstrates that calcium is invariably needed at high concentrations in annexin V staining. If the cells need to be stained with Annexin V, the cell buffer has to be changed to an Annexin V binding buffer which consists of 0.1M HEPES (pH 7.4), 1.4M NaCl, and 25 mM CaCl2. During the buffer change, the status of cells could change and the dead cells could be lost during centrifugation. If the samples need to be fixed for post-staining, the Annexin V staining PS positive cell might not remain. Thus, a new generation of calcium independent PS binding agent is needed.

Apo-15 was recently reported to selectively recognize the apoptotic and dead cells by binding negatively charged phospholipids exposed on apoptotic and dead cell surface in a calcium-independent manner for detecting the PS positive cells by flow cytometry and microscopy (Barth et al., *A fluorogenic cyclic peptide for imaging and quantification of drug-induced apoptosis*. Nature Communications. 2020; 11, Article number: 4027). Apo-15 is a cyclic peptide comprising the sequence of SEQ ID NO: 1 [RKKWFW(BODIPY) G], wherein each of said amino acid Arg, Lys, Trp, Phe, Gly contains a carboxyl (COOH) and an amine (NH2) group, said Trp(BODIPY) is an Fmoc-labelled amino acid of Trp attached to a BODIPY (4,4-difluoro-4-bora-3a,4a-diaza-s-indacene) dye through a spacer-free C—C linkage (Subiros-Funosas et al., *A Trp-BODIPY cyclic peptide for fluorescence labelling of apoptotic bodies*. Chem. Commun. 2017; 53945-948; and Mendive-Tapia et al., *Spacer-free BODIPY fluorogens in antimicrobial peptides for direct imaging of fungal infection in human tissue*. Nature Communications. 2016; 7, 10940; and Mendive-Tapia et al., *Preparation of a Trp-BODIPY fluorogenic amino acid to label peptides for enhanced live-cell fluorescence imaging*. 2017. Nat Protoc. August; 12(8):1588-1619). The Trp(BODIPY) functions as a single element to be detected for imaging and remains Trp native property. Said Arg and Lys not only contain an amine and a carboxyl group, but also contain second amine group on side chain. Since Arg and Lys have positive charges which are the key elements to bind negatively charged phosphatidylserine, the second amine group is not considered for chemical labelling. So, Apo-15 does not have available functional group for coupling with commonly used fluorophores, such as Alexa dye. If changing different exciting and emission BODIPY dye, a new Trp(BODIPY) has to be made before synthesizing the new format of Apo-15. To date, there is only one format of Trp(BODIPY) available on market which is commercially named as Apotracker Green with excitation at 500 nm and emission at 520 nm for flow cytometry application. Apo-15 has some limitations in selecting different formats of fluorophore for multicolor flow cytometry and multiplex imaging. Therefore, an advanced new PS binding compound which can couple with different formats of fluorophores is needed.

Dead cell removal is a fast and straightforward way of eliminating dead cells from cell culture to tissue preparations. The most common method of depleting PS positive cells is using annexin V conjugated particles or using biotinylated Annexin V to label the PS positive cells followed by binding streptavidin conjugated particles in calcium dependent manner. By using the buffer containing high concentration of calcium, the cells can form aggregates which affect the yield of the live cell. MojoSort™ Human Dead Cell Removal Kit and MojoSort™ Mouse Dead Cell Removal Kit (BioLegend, Catalog number: 480159 and 480157) were recently launched on the market. These two kits deplete the PS positive cells without $Ca^{2+}$, however, it requires an additional step to pre-incubate Apo-Monomer recombinant protein and streptavidin nanobeads for 5 minutes prior contacting with cells. Therefore, one step calcium free PS positive cells removal kit is highly desired in order to shorten the experiment process with high purity and yield. Apo-15 is able to bind PS positive cells, but it does not have available functional group to conjugate with solid phase carries. Therefore, an advanced new PS binding compound having functional group for conjugation with solid phase carrier to deplete PS positive cells is needed.

Single-cell RNA sequencing (scRNA-seq) technologies have become the state-of-the-art approach for simultaneously measuring of surface protein and gene expression within single cells using oligo conjugated antibodies which offer high-resolution snapshots of complex cell populations and better understanding of the function on an individual cell in the context of its microenvironment (Eberwine et al., *The promise of single-cell sequencing*. Nature Methods. 2014; 11, pages 25-27; and Pennisi et al., *Chronicling embryos, cell by cell, gene by gene*. Science. 2018; Vol 360, Issue 6387; and Saliba et al., *Single-cell RNA-seq: advances and future challenges*. Nucleic Acids Res. 2014; 18; 42(14): 8845-8860). The single cell sequencing technologies require four main steps: (1) Isolation of single cells from a cell population into each droplet; (2) Extraction, processing and amplification of the genetic material of each isolated cell; (3) Preparation of a "sequencing library" including the genetic material of an isolated cell; (4) Sequencing of the library using a next-generation sequencer (Pennisi et al., *Chronicling embryos, cell by cell, gene by gene*. Science. 2018; Vol 360, Issue 6387). Each droplet carries a DNA "barcode" that uniquely labels the cDNAs derived from a single cell. Once reverse transcription is completed, the cDNAs from many cells are mixed together for sequencing and the transcripts from a particular cell can also be identified by the unique barcode.

Single-cell RNA sequencing is becoming widely used across biological disciplines, such as immunology, oncology, and developmental biology. However, the whole process from cell preparation to data analysis is time consuming with high cost. Generally, scRNA-seq experiments can generate a portion of low-quality data from the cells that are broken or dead or mixed with multiple cells, which will hinder the downstream analysis and may lead to misinterpretation of the data (Chen et al., *Single-Cell RNA-Seq Technologies and Related Computational Data Analysis*. Front Grnet. 2019; 10:317; and Deleersnijder et al., *Current Methodological Challenges of Single-Cell and Single-Nucleus RNA-Sequencing in Glomerular Diseases*. J Am Soc Nephrol. 2021; August; 32(8):1838-1852). Due to technical limitations and biological factors, the significant challenges remain in the analysis, integration, and interpretation of single-cell omics data such as how to identify the non-viable cells contaminations in single-cell sequencing approaches.

An innovative approach is needed to make the PS binding agent labelled with oligo containing unique barcode as an identifier of PS positive cells which can discriminate PS positive cells from live cells. In this way, the bioinformatic scientist will be able to filter the PS positive cells and only analyze the live cells, which can improve the accuracy and effectiveness of cellular indexing of transcriptomes and epitopes by sequencing (CITE-Seq). Generally, the reagent containing oligo needs at least 0.1 mM EDTA (ethylenediaminetetraacetic acid) to prevent nuclease digestion of the DNA. When oligo contacts with the cells, EDTA will chelate calcium in the cells buffer which will affect Annexin V PS binding function. Thus, a novo calcium independent PS binding agent coupling with oligo containing unique barcode for PS positive cells is highly desired.

Accordingly, there is room in the art of modifying or changing the structure of existing compound by using substituent amino acid containing specific functional group to expand the applications for discriminating and eliminating PS cells.

SUMMARY OF THE INVENTION

The present invention generally relates to the methods of making the phosphatidylserine (PS) binding compound derivative and the fusion of PS binding compound with an arm compound. The present invention also relates to the methods of using PS binding compound derivative and the fusion of PS binding compound with an arm compound to detect PS positive cells for multicolor flow cytometry and multiplex imaging, and to deplete the PS positive cells in separation system, and to discriminate positive cells from live cells in Single-cell RNA sequencing.

A phosphatidylserine (PS) binding compound, wherein the residue Trp(BODIPY) at position 6 of amino acid sequence of SEQ ID NO: 1 has been substituted with a natural amino acid Trp to remove the fluorescence, and wherein the residue Gly at position 7 has been substituted with an amino acid Cys, or a synthetic amino acid propargylglycine (Pra).

The present invention provides for a PS binding compound derivative comprising the sequence of SEQ ID NO: 2 [RKKWFWC] (Item-2), wherein the amino acid Cys is used to provide a thiol group for coupling with maleimide-containing Tag by using thiol-maleimide reaction.

The PS binding compound derivative Item-2 comprising the sequence of SEQ ID NO: 2 was synthesized and validated by Mass Spectrometry. The Item-2 was coupled with maleimide-containing fluorophore wherein the fluorophore was maleimide-containing Atto 647. The Atto 647 maleimide coupled Item-2 (Atto 647 Item-2) was validated by Mass Spectrometry, flow cytometry and fluorescent microscope.

The experimental results illustrate that the PS binding compound derivative Item-2 comprising the sequence of SEQ ID NO: 2 not only remains the PS binding features but also enables to provide thiol group for coupling with maleimide-containing fluorophore for multicolor flow cytometry and multiplex imaging.

The PS binding compound derivative Item-2 comprising the sequence of SEQ ID NO: 2 contains one thiol group so as to allow the PS binding compound derivative to couple with one maleimide-containing Tag, wherein said Tag is a detectable unit including but not limited to fluorophore, solid phase carrier, oligo, biotin, avidin, protein, enzyme, and radionuclide. In addition, the Tag may also be a maleimide-containing bifunctional linker, wherein maleimide-containing bifunctional linker includes but not limited to maleimide-Pol-Maleimide, maleimide-Pol-thiol, maleimide-Pol-azide, maleimide-Pol-alkyne, maleimide-Pol-NHSter, maleimide-Pol-amine, and maleimide-Pol-COOH; wherein said maleimide is used to link with thiol group in the Cys of Item-2, wherein another functional group in said maleimide-containing bifunctional linker is used for chemical labelling; wherein said Pol is a polymer including but not limited to $(PEG)_n$, $(PEO)_n$, $(\varepsilon\text{-Caprolactam})_n$, $(CH2)_n$, and $[(PEG)_n(CH2)_n]$, wherein n is an integer from 1 to 60, preferably 1 to 24, more preferably 1 to 12.

In present invention, PS binding compound derivative Item-2 comprising the sequence of SEQ ID NO: 2 provides thiol group for coupling with maleimide-containing Tag. In addition, Tag may also be a maleimide-containing bifunctional linker, which may provide more functional groups such as amine, NHSter, thiol, maleimide, alkyne, azide, and carboxyl group for chemical labelling.

The present invention provides for a PS binding compound derivative comprising the sequence of SEQ ID NO: 3 [RKKWFWPra] (Item-3) wherein the synthetic amino acid Pra is used to provide an alkyne group for coupling with an azide-containing Tag by using azide-alkyne reaction.

The PS binding compound derivative Item-3 comprising the sequence of SEQ ID NO: 3 was synthesized and coupled with azide-containing fluorophore, wherein the fluorophore was azide contained Fluorescein (FITC). The PS binding compound derivative Item-3 was validated by Mass Spectrometry, and azide contained FITC coupled Item-3 (FITC Item-3) was valideted by flow cytometry.

The experimental results illustrate that the PS binding compound derivative Item-3 comprising the sequence of SEQ ID NO: 3 not only remains the PS binding features but also enables to provide an alkyne group for coupling with azide-containing fluorophore for multicolor flow cytometry.

The PS binding compound derivative Item-3 comprising the sequence of SEQ ID NO: 3 contains one alkyne group so as to allow the PS binding compound derivative Item-3 to couple with an azide-containing Tag, wherein said Tag is a detectable unit including but not limited to fluorophore, solid phase carrier, oligo, biotin, avidin, protein, enzyme, and radionuclide. In addition, the Tag may be an azide-containing amino acid including but not limited to azido-Lysine, azido-propargylglycine, azido-L-propargylglycine, azido-histidine, azido-tryptophan, azido-phenylalanine, azido-arginine, azido-glutamine, azido-glycine, azido-valine, and azido-alanine, wherein said azide group is used to link with alkyne in Pra of Item-3, wherein said amino acid having functional group is used for chemical labelling. Furthermore, the Tag may also be an azide-containing bifunctional linker including but not limited to azido-Pol-maleimide, azido-Pol-thiol, azido-Pol-alkyne, azido-Pol-azide, azido-Pol-amine, azido-Pol-NHSter, and azido-Pol-COOH, wherein azide group is used to link with Pra of Item-3 and another functional group in said azide-containing bifunctional linker is for chemical labelling, wherein said Pol is a polymer used as a linker including but not limited to $(PEG)_n$, $(PEO)_n$, $(\varepsilon\text{-Caprolactam})_n$, $(CH2)_n$, and $[(PEG)_n(CH2)_n]$, wherein n is an integer from 1 to 60, preferably 1 to 24, more preferably 1 to 12.

In present invention, the PS binding compound derivative Item-3 comprising the sequence of SEQ ID NO: 3 provides an alkyne group for coupling with azide-containing Tag. In addition, the Tag may also be an azide-containing amino acid or an azide-containing bifunctional linker, which may provide more functional groups such as amine, NHSter, thiol, maleimide, alkyne, azide, and carboxyl group for chemical labelling.

The present invention provides for a fusion of PS binding compound with an arm compound comprising the sequence of SEQ ID NO: 5 [RKKWFWPra-Xa1(azido)-Xa2-$(Pol\text{-}Xa3)_m$], (Item-5) wherein the arm compound comprising the sequence of SEQ ID NO: 4 [Xa1(azido)-Xa2-$(Pol\text{-}Xa3)_m$] (Item-4) is linked with the Pra in PS binding compound derivative Item-3 comprising the sequence of SEQ ID NO: 3 to provide at least one functional group for coupling with at least one functional group-containing Tag.

The fusion comprising the sequence of SEQ ID NO: 5 coupled with functional group containing fluorophore was synthesized and validated by Mass Spectrometry, wherein said variable amino acid [Xa1(azido)] was Lys(azido), said variable amino acid (Xa2) was Lys, said variable $(Pol\text{-}Xa3)_m$ was $(PEG4\text{-}Lys)_3$ wherein said PEG is Fmoc-NH-PEG-COOH, wherein said three Lys in $(PEG4\text{-}Lys)_3$ provides three amine groups to couple with three NHSter-containing fluorophores, said functional group containing fluorophore was NHSter-containing Fluorescein (FITC). The NHSter-containing FITC coupled Item-5 (FTIC Item-5) was validated by flow cytometry.

The experimental results illustrate that the fusion Item-5 comprising the sequence of SEQ ID NO: 5 not only remains PS binding features but also enables to provide three amine groups to couple with three NHSter-containing fluorophores for multicolor flow cytometry.

The fusion Item-5 comprising the sequence of SEQ ID NO: 5 described herein contains an arm compound Item-4 comprising the sequence of SEQ ID NO: 4, wherein Xa1 is an azide-containing amino acid includes but not limited to azido-Lysine, azido-propargylglycine, azido-L-propargylglycine, azido-histidine, azido-tryptophan, azido-phenylalanine, azido-arginine, azido-glutamine, azido-glycine, azido-valine, and azido-alanine, wherein said azide group is used to link with alkyne in Pra of Item-3, wherein said amino acid having functional group is used for linking with Xa2; said Xa2 is an amino acid used as a linker to link with Xa1 and (Pol-Xa3) including but not limited to Lys, Arg, His, Ser, Thr, Cys, Asn, Gin, Pra, and Tyr; said $(Pol\text{-}Xa3)_m$ is an independent variable used to link with Xa2, wherein Pol is a polymer used as a linker including but not limited to $(PEG)_n$, $(PEO)_n$, $(\varepsilon\text{-Caprolactam})_n$, $(CH2)_n$, and $[(PEG)_n(CH2)_n]$; said Xa3 is an amino acid having amine, or thiol, or alkyne functional group for coupling with NHSter or maleimide or azide group containing Tag, wherein the amino acid includes but not limited to Lys, Arg, His, Met, Cys, and Pra. The number of polymers can be selected and indicated by n, wherein n is an integer from 1 to 60, preferably 1 to 24, more preferably 1 to 12. The variable m is the number of (Pol-Xa3) wherein m is an integer from 1 to 10.

In present invention, the fusion of PS binding compound with an arm comprising the sequence of SEQ ID NO:5 is able to provide amine, or thiol, or alkyne functional group to couple with NHSter, or maleimide, or azide-containing Tag, wherein said Tag is used as a detectable unit including but not limited to fluorophore, oligo, solid phase carrier, biotin, avidin, protein, enzyme, radionuclide. In addition, the functional group provided by fusion Item-5 can be selected for chemical labelling and the number of functional groups provided by fusion Item-5 is adjustable.

The present invention provides for a fusion of PS binding compound with an arm compound comprising the sequence of SEQ ID NO: 7 [RKKWFWPra-Xa1(azido)-Xa2-Pol-Xa3] (Item-7) wherein an arm compound comprises the sequence of SEQ ID NO: 6 [Xa1(azido)-Xa2-Pol-Xa3] (Item-6) was linked to the Pra in the PS binding compound derivative Item-3 comprising the sequence of SEQ ID NO: 3 to provide a functional group for coupling with a functional group containing Tag.

The fusion Item-7 comprising the sequence of SEQ ID NO: 7 was synthesized and validated by Mass Spectrometry, wherein the variable Xa1(azido) was Lys(azido), and the variable Xa2 was Lys, and the Pol was PEG12, and PEG was Fmoc-NH-PEG-COOH and the variable Xa3 was Cys in order to provide an alkyne group for coupling with a maleimide-containing Tag.

The fusion Item-7 was conjugated with maleimide-containing protein fluorophore R-phycoerythrin (PE) (PE Item-7) and validated by flow cytometry.

The fusion Item-7 was conjugated with maleimide coated magnetic particles and validated by using the magnetic separation system.

The fusion Item-7 was coupled with maleimide-containing oligo (Poly T oligo Item-7) comprising the sequence of SEQ ID NO: 8 and validated by flow cytometry.

The experimental results illustrate that the fusion of PS binding compound with an arm Item-7 comprising SEQ ID NO: 7 is able to couple with maleimide-containing protein fluorophore PE for multicolor flow cytometry, to couple with maleimide coated magnetic particle for depleting PS positive cells, and to couple with maleimide-containing oligo for binding the PS positive cells, wherein the oligo comprises a PCR handing sequence, a unique DNA barcode sequence for PS positive cells and a capture sequence, which may discriminate the positive cells from live cells in Single-cell RNA sequencing.

The fusion Item-7 comprising the sequence of SEQ ID NO: 7 described herein contains an arm comprising the sequence of SEQ ID NO: 6 wherein Xa1 is an azide-containing amino acid including but not limited to azido-Lysine, azido-propargylglycine, azido-L-propargylglycine, azido-histidine, azido-tryptophan, azido-phenylalanine, azido-arginine, azido-glutamine, azido-glycine, azido-valine, and azido-alanine, wherein said azide group is used to link with alkyne in Pra of Item-3, wherein said amino acid having functional group is used for linking with Xa2; said Xa2 is an amino acid used as a linker to link with Xa1 and Pol, wherein the amino acid includes but not limited to Lys, Arg, His, Ser, Thr, Cys, Asn, Gln, Pra, and Tyr; said Pol is a polymer containing amine and carboxyl group used as a linker to link with Xa2 and Xa3 including but not limited to $(PEG)_n$, $(PEO)_n$, $(\varepsilon\text{-Caprolactam})_n$, $(CH2)_n$, and $[(PEG)_n (CH2)_n]$, wherein n is the number of polymer wherein n is an integer from 1 to 60, preferably 1 to 24, more preferably 1 to 12; said Xa3 is an amino acid containing amine, or thiol, or alkyne functional group for coupling with NHSter or maleimide or azide-containing Tag, wherein said amino acid includes but not limited to Cys, Pra, Met, Lys, Arg, and His.

In present invention, the fusion of PS binding compound with an arm compound Item-7 is able to provide amine, or thiol, or alkyne functional group to couple with NHSter, or maleimide, or azide-containing Tag, wherein said Tag is used as a detectable unit including but not limited to fluorophore, oligo, solid phase carrier, biotin, avidin, protein, enzyme, radionuclide. In addition, the functional group provided by fusion Item-7 can be selected for chemical labelling. The length of the linker can be adjusted which may help to couple with large size Tag.

In present invention, the PS binding compound derivative Item-2 and Item-3, and the fusion Item-5 and Item-7 provide functional group to couple with functional group containing fluorophore for multicolor flow cytometry and multiplex imaging, to couple with functional group containing solid phase carrier for depleting PS positive cells, and to couple with functional group containing oligo for binding the PS positive cells, which may discriminate PS positive cells from live cells by identifying the unique DNA barcode sequence in Single-cell sequencing, wherein said oligo comprises a PCR handing sequence, a unique DNA barcode sequence for PS positive cells and a capture sequence.

Other advantages and novel features of present invention will become apparent from the following detailed description of various non-limiting embodiments of present invention when considered in the conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document have the later effective date shall control.

BRIEF DESCRIPTION OF THE DRAWINGS

For a more complete understanding of present invention, reference should now be made to the embodiments illustrated in great detail in the accompanying drawings (figures) and described below by way of examples of the invention wherein:

FIG. 1A-2 shows the molecular weight of cyclized PS binding compound derivative comprising the sequence of SEQ ID NO: 2 measured by Mass Spectrometry.

FIG. 1A-3 shows the molecular weight of Atto 647 Item-2 measured by Mass Spectrometry.

FIG. 2A-1 shows the molecular weight of the PS binding compound derivative comprising the sequence of SEQ ID NO: 3 (Item-3) in linear measured by Mass Spectrometry.

FIG. 2A-2 shows the molecular weight of the cyclized PS binding compound derivative comprising the sequence of SEQ ID NO: 3 measured by Mass Spectrometry.

DETAILED DESCRIPTION OF THE INVENTION

Figures 1, 1A:
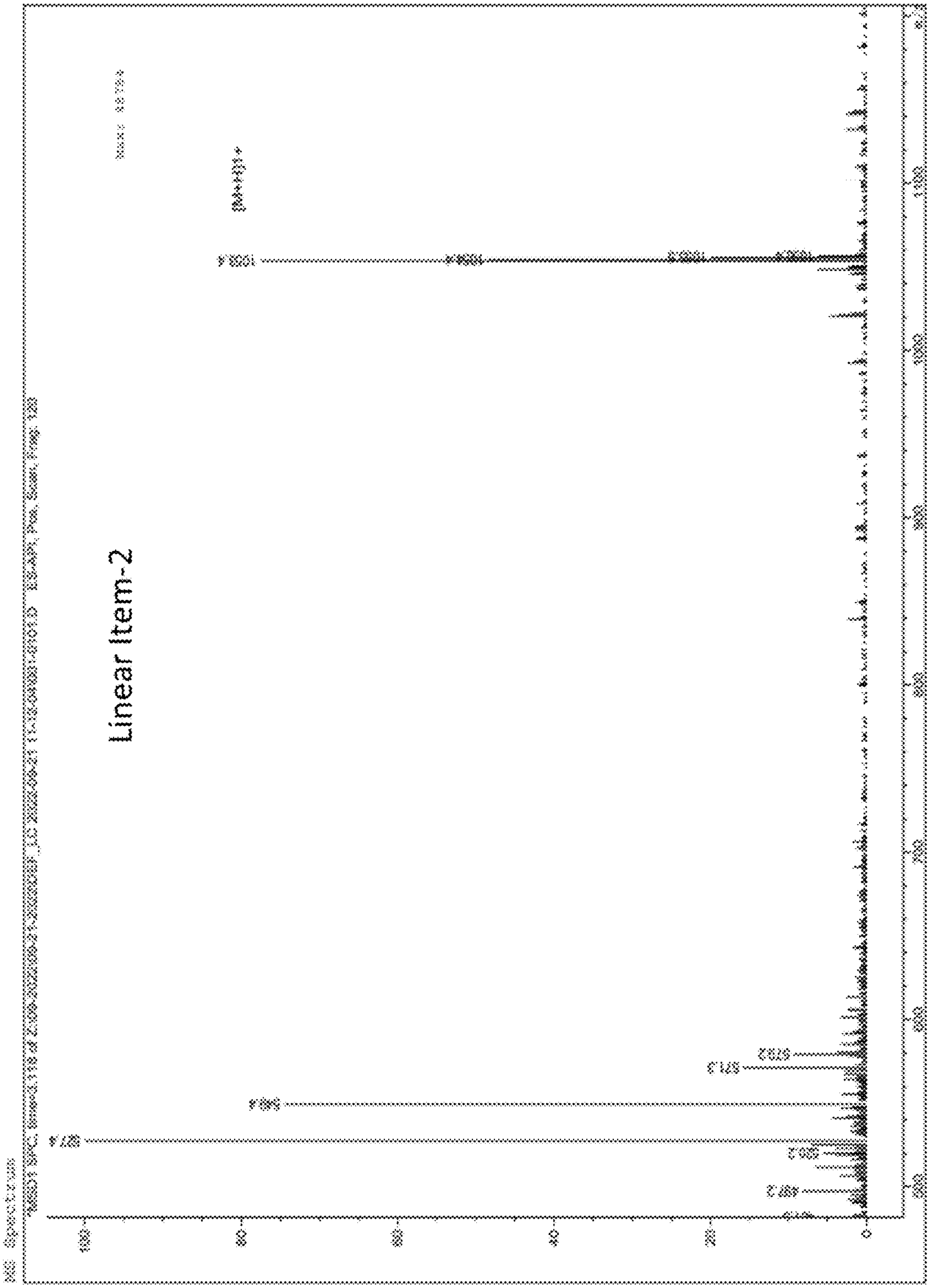
FIG. 1A-1 shows the molecular weight of the PS binding compound derivative comprising the sequence of SEQ ID NO: 2 (Item-2) in linear measured by Mass Spectrometry.

The following detailed description illustrates certain preferred embodiments of the invention and is thus only representative and does not depict the actual scope of the invention. It is to be understood that this invention is not limited to some specific embodiments described and is not limited to particular methodologies, protocols and reagents described herein as these may vary.

All scientific and technical terms used herein have meanings commonly used in the art unless otherwise specified. The definitions provided herein are to facilitate understanding of certain terms used frequently herein and are not meant to limit the scope of the present disclosure.

As used herein, "conjugate", "conjugation", "labelled", "couple", "coupling", "coupled", "link", "linking", "linked", "linkage" is used interchangeably. These terms refer to the joining together of two more elements or components or molecular by chemical conjugation. Methods of chemical conjugation (e.g., using click chemistry) are known in the art. As used herein, the term "conjugated" or "labelled" or "coupled" refers to the co-linear, covalent linkage or attachment of two or more proteins, fluorescence dye, oligonucleotides/oligos, avidin, streptavidin, enzyme, solid phase carrier (particle, microbubble) fragments thereof via peptide backbones.

As used herein, "PS binding compound" is a compound which specifically binds to phosphatidylserine (PS). In the context of the present invention, a PS binding compound is understood to be capable of binding PS exposed on the outer leaflet of the cell membrane on apoptotic cells or dying cells, dead cells or cell debris, activated platelets, and extracellular vesicles (EV).

Phosphatidylserine (PS) Binding Compound

The reference cyclic amphipathic peptide Apo-15 comprises the sequence of SEQ ID NO: 1 (Item-1), wherein Arg and Lys are hydrophilic with positive charged amino acids, Trp and Phe and Gly are hydrophobic with neutral charged amino acids. Said each amino acid in Apo-15 sequence contains an amine (NH2) group and a carboxyl (COOH) group. Said amino acids in Apo-15 sequence, Arg also has one complex side chain (CH2-CH2-CH2-NH—CNH—NH2) and Lys also has a long side chain with four CH2 and it ends in an amino group. Since Arg and Lys have positive charges which are the key elements to bind negatively charged PS, the amine group on side chain is not considered for chemical labelling. Said Trp(BODIPY) is Trp-based fluorogenic amino acid Fmoc-Trp(C2-BODIPY)-OH containing a BODIPY (4,4-difluoro-4-bora-3a,4a-diaza-s-indacene) fluorogenic core, wherein BODIPY attaches to Trp via a spacer-free C—C linkage. The Gly is used to facilitate head-to-tail cyclization.

The Apo-15 is a new PS binding agent and like commonly used PS binding reagent Annexin V to detect the PS positive cells by using flow cytometry or fluorescent microscope. The advantage of this agent is that the Apo-15 binds PS in calcium independent manner. As an agent for imaging, it generally needs to have different formats of fluorophores to provide options in selecting different fluorophores for multicolor flow cytometry or multiplex imaging. To date, Apo-15 only has one format available with excitation at 500 nm and emission at 520 nm for multicolor flow cytometry. Since Apo-15 does not have available functional group for coupling with commonly used fluorophores, a new derivative of Trp(BODIPY) in different excitation and emission is required before synthesizing a new format of Apo-15. In order to meet market demands, the PS binding agent should have functional group which is able to couple with different formats of fluorophores by using standard well illustrated conjugation methods to keep the manufacturing process simple with low cost.

In order to overcome the limitations of Apo-15 and make it possible to couple with different formats of fluorophores and remain the PS binding abilities, modifications and changes have to be made in the structure of the cyclic peptides by using substituent amino acid to replace certain amino acids in the sequence without appreciable loss of activity. Substitution of amino acids can be considered on the basis of the relative similarity of the amino acid, for example, their hydrophobicity, hydrophilicity, and charge. To achieve the goal, a new approach in present invention comprises: (1) keeping Apo-15 PS binding ability; (2) removing fluorogenic amino acid Trp(BODIPY); (3) creating at least one additional functional group for chemical labelling.

"PS binding compound derivative" as used here refers to a phosphatidylserine (PS) binding compound, wherein the residue Trp(BODIPY) at position 6 of amino acid sequence of SEQ ID NO: 1 (Apo-15) has been substituted with a natural amino acid Trp to remove the fluorescence, and wherein the residue Gly at position 7 has been substituted with an amino acid Cys, or a synthetic amino acid propargylglycine (Pra).

The present invention provides for a PS binding compound derivative comprising the sequence of SEQ ID NO: 2 (Item-2), wherein the amino acid Cys is used to provide a thiol group for coupling with a maleimide-containing Tag by using thiol-maleimide reaction.

The method of making PS binding compound derivative Item-2 comprises: (1) using natural amino acid Trp to replace the fluorogenic amino acid Trp(BODIPY) at position 6 of in the amino acid sequence of SEQ ID NO: 1 in order to remove the fluorescence and remain the native property of the Trp; (2) using amino acid Cys to replace the amino acid Gly at position 7 in the amino acid sequence of SEQ ID NO: 1 wherein said Cys contains three functional groups including an amine group and a carboxyl group for facilitating head-to-tail cyclization, and a thiol group on the side chain for chemical labelling by using thiol-maleimide reaction. The thiol-maleimide reaction is a simple and rapid reaction, which is currently one of the most popular methods in bioconjugation technology.

The PS binding compound derivative Item-2 coupling with maleimide-containing fluorophore is used as an example for making and using Item-2, wherein maleimide-containing fluorophore Atto 647 was used to couple with Item-2 by using thiol-maleimide reaction and the fluorophore was used as a detectable unit to be detected by flow cytometry or fluorescent microscope for multicolor flow cytometry and multiplex imaging.

The PS binding compound derivative Item-2 was synthesized and validated by Mass Spectrometry. The observed molecular weight of cyclic peptide of Item-2 is 1034.4 g/mole (see FIG. 1A-2) which subtracts one $H_2O$ molecular weight from the molecular weight 1052.4 g/mole of linear Item-2 (see FIG. 1A-1). The experimental results indicate that Item-2 was successfully synthesized. Also as shown in FIG. 1A-3, Item-2 was successfully conjugated with Atto 647 maleimide (Atto 647 Item-2) by using thiol-maleimide reaction.

Whether an agent is considered to be a PS binding agent or to have a PS binding activity, it can be determined by using a flow cytometer to detect the PS binding activity of said agent which has been illustrated in the art. Thereby, PS positive cells can be used in such an assay, wherein the number of stained cells may be compared to the reference agent Apotracker Green and/or Annexin V, in accordance with the present invention.

To validate the staining pattern and the frequencies of PS positive dying cells and dead cells, one day old C57BL/6 mouse thymocytes were side by side stained with Atto647

Item-2, or Apotracker Green (commercial name of Apo-15) in PBS without $Ca^{2+}$ or Alexa 647 Annexin V in Annexin binding buffer. Sytox Blue is an impermeant blue-emitting nucleic acid indicator which is used for indicating the dead cells. As shown in FIG. 1B, the Item-2 Sytox are live cells shown in Q4, the Item-$2^+$ Sytox are dying cells with intact membrane shown in Q1 and the Item-$2^+$Sytox$^+$ are dead cells shown in Q2. The staining pattern and the frequencies of PS positive dying cells and dead cells stained with Atto 647 Item-2 or Apotracker Green or Alexa 647 are comparable to each other.

When the 2 days IL-4 stimulated U937 cells were simultaneously stained with Atto 647 Item-2 and Apotracker Green, the frequencies of PS positive dying cells and dead cells stained with Atto 647 Item-2 and Apotracker Green are very similar. Also, the cells stained with Atto 647 Item-2 and Apotracker Green show diagonal distribution in two-parameter density plots (see FIG. 1C).

To further study the relationship between the PS positive dying cells and dead cells stained with Atto 647 Item-2 and Apotracker Green, the correlation coefficient is used. Table I shows the frequencies of live cells, PS positive dying cells and dead cells from four independent experiments, in which different types of cells were simultaneously stained with Atto 647 Item-2 and Apotracker Green at different concentrations in PBS without $Ca^{2+}$. As shown in Table 2, the correlation coefficients are very close to 1.0, which means that the live cells, and PS positive dying cells and dead cells stained by Atto 647 Item-2 and Apotracker Green show very strong positive correlation and have an almost perfect linear relationship. The experimental results verified that the PS positive dying cells and dead cells stained with Atto 647 Item-2 and Apotracker Green are highly related.

To validate if Item-2 stained PS positive cells are fixable for post-staining, the fresh and 2 days IL-4 stimulated U937 cells in PBS without $Ca^{2+}$, were stained with Atto 647 Item-2 followed by 2% of Paraformaldehyde (PFA) fixation. As shown in FIG. 1D, the staining pattern and the frequencies of the cells in Q1, Q2, Q3 and Q4 are similar before and after fixation. The staining fluorescence intensity is slightly lower on fixed cells than on the cells without fixation because there is one wash after fixation. The experimental results illustrate that Atto 647 Item-2 stained PS positive dying cells and dead cells are fixable and support that Item-2 binding PS is $Ca^{2+}$ independent.

To further validate if the PS cells stained with Atto 647 Item-2 are visualized by microscope, the adherent human lung adenocarcinoma cell line (Calu-6) cells were simultaneously stained with Atto 647 Item-2, and Calcein AM, and Fixable viability dye-405. As shown in FIG. 1E, Calcein $AM^+$ Atto 647 Item-2-Fixable viability dye-405-cells are live cells, Calcein $AM^{Weak/-}$Atto 647 Item-$2^+$ Fixable viability dye-$405^-$ are dying cells, and Calcein AM Atto 647 Item-$2^+$ Fixable viability dye-$405^+$ are dead cells. Calcein AM is membrane-permeable live-cell labeling dye which labels live cells. Fixable viability dye 405 reacts with protein amine groups in compromised cell membrane which labels dead cells. The experiment results show that Atto 647 Item-2 can be used for multiplex imaging.

As described elsewhere herein, the experimental results illustrate that the PS binding compound derivative Item-2 has been successfully synthesized in present invention. Said Item-2 not only remains PS binding ability but also provides a thiol group for coupling with maleimide-containing fluorophore, which provides more options in selecting different fluorophores for multicolor flow cytometry and multiplex imaging. As the different maleimide-containing fluorophores are commercially available and the conjugation method is well illustrated, the risk of manufacturing process and cost shall be reduced.

The PS binding compound derivative Item-2 couples with maleimide-containing Tag, wherein maleimide-containing Tag may also be a maleimide-containing bifunctional linker including but not limited to maleimide-Pol-Maleimide, maleimide-Pol-thiol, maleimide-Pol-azide, maleimide-Pol-alkyne, maleimide-Pol-NHSter, maleimide-Pol-amine, and maleimide-Pol-COOH; wherein said maleimide is used to link with thiol group in the Cys of Item-2, wherein another functional group of thiol, or maleimide, or azide, or alkyne, or NHSter, or amine, or carboxyl in the maleimide-containing bifunctional linker is used for chemical labelling; wherein the linker may be a polymer or amino acid, wherein said polymer includes $(PEG)_n$, $(PEO)_n$, (ε-Caprolactam)$_n$, $(CH2)_n$, and $[(PEG)_n(CH2)_n]$, wherein the n is the number of polymers, wherein n is an integer from 1 to 60, preferably 1 to 24, more preferably 1 to 12.

In present invention, PS binding compound derivative Item-2 comprising the sequence of SEQ ID NO: 2 provides a thiol group for coupling with maleimide-containing Tag, wherein the Tag is used as a detectable unit including but not limited to a fluorophore, a solid phase carrier, an oligo, a biotin, an avidin, a protein, an enzyme, and a radionuclide. In addition, when said Tag is maleimide-containing bifunctional linker, the maleimide-containing bifunctional linker may provide amine, or NHSter, or carboxyl, or thiol, or maleimide, or alkyne, and azide group for chemical labelling.

In present invention, when the functional group containing fluorophore, the fluorophore may be any one of fluorescent dyes. It includes but not limited to PE, APC, PerCp and their tandem dyes such as Cy3, Cy5, Cy7, A596, A640, A750 and A810, 350/405/488/647/594/700/750, DL545/570/585/590/685, FITC, NIR dye and Pacific blue, Pacific Orange, BV421, BV510, BV605, BV650, BV710, Atto 390, Atto 425, Atto465, Atto 488, Atto495, Atto520, Atto532, Atto 550, Atto 565, Atto 590, Atto 594, Atto 610, Atto 620, Atto633, Atto635, Atto647, Atto655, Atto 680, Atto700, Atto725, functional group containing BODIPY, and bioluminescent. Such fluorophores can be used as a detectable unit to be detected by flow cytometry and fluorescent microscope.

The present invention provides for another PS binding compound derivative comprising the sequence of SEQ ID NO: 3 (Item-3), wherein the synthesized amino acid Pra is used to provide an alkyne group for coupling with azide-containing Tag by using azide-alkyne reaction.

The method of making PS binding compound derivative Item-3 comprises: (1) using natural amino acid Trp to replace fluorogenic amino acid Trp(BODIPY) at position 6 of the amino acid sequence of SEQ ID NO: 1 in order to remove the fluorescence and remain the native property of the Trp; (2) using the synthetic amino acid Pra to replace the amino acid Gly at position 7 of the amino acid sequence of SEQ ID NO: 1, wherein said Pra is a Fmoc protected Gly derivative which contains an amine group and a carboxyl group for facilitating head-to-tail cyclization and an alkyne group for azide-alkyne reaction which confers a high level of flexibility when incorporating into polypeptides.

The PS binding compound derivative Item-3 coupling with azide-containing fluorophore is used as an example for making and using Item-3, wherein azide-containing fluorophore Fluorescein azide was used to couple with Item-3 by using azide-alkyne reaction. The fluorophore is used as a detectable unit to be detected by flow cytometry for multi-color flow cytometry The PS binding compound derivative Item-3 was synthesized and the molecular weight was measured by Mass Spectrometry. The observed molecular weight of linear Item-3 is 1044.5 g/mole as shown in FIG. 2A-1. The observed molecular weight of cyclic Item-3 is 1026.5 g/mole because one $H_2O$ molecular weight is eliminated during head-tail cyclization (see FIG. 2A-2). The experimental results confirmed that Item-3 was successfully synthesized. Fluorescein azide was coupled with Item-3 and Fluorescein azide coupled Item-3 (FITC Item-3) was validated by flow cytometry.

Figures 1, 2A:
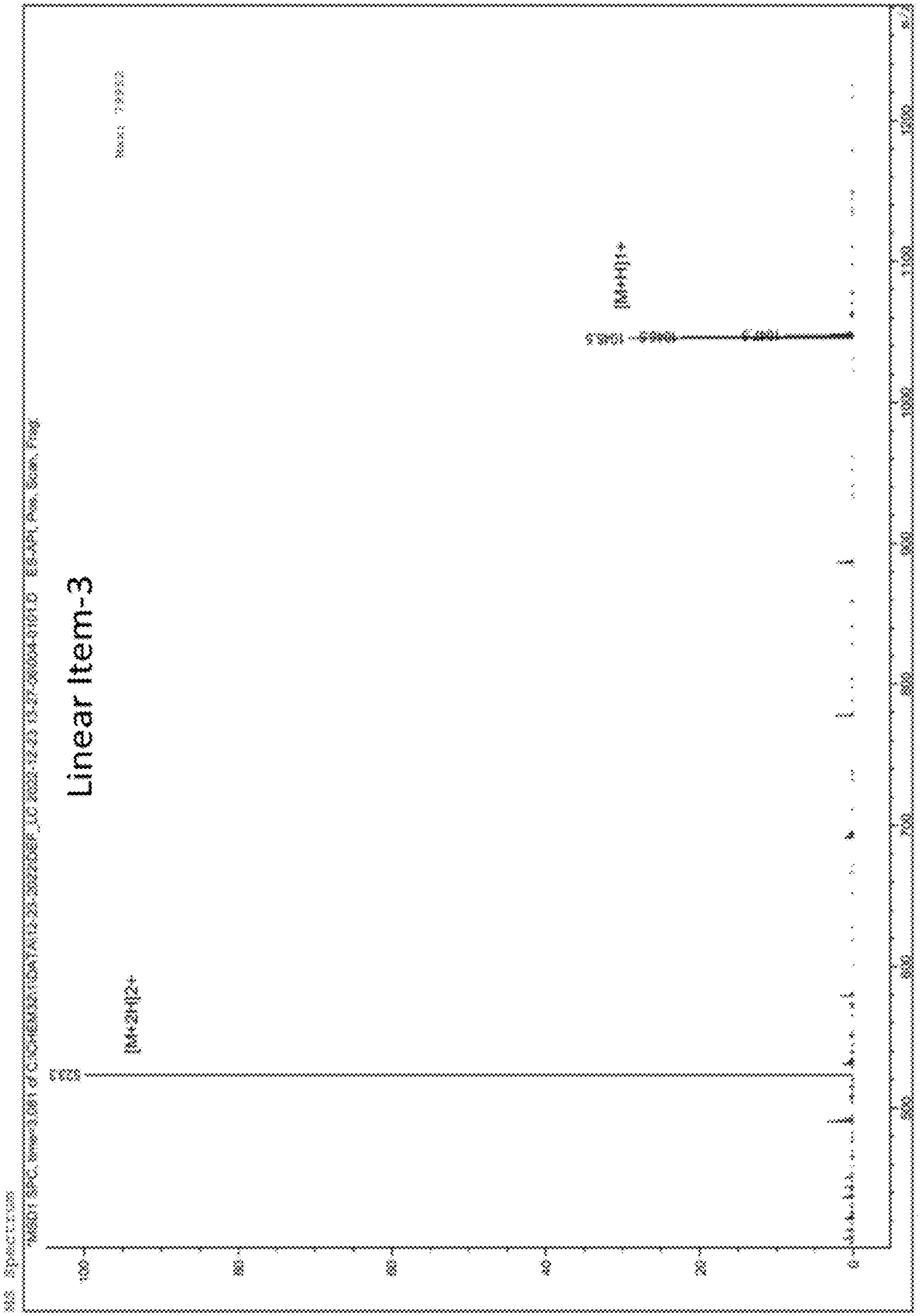
Figures 2, 2A:
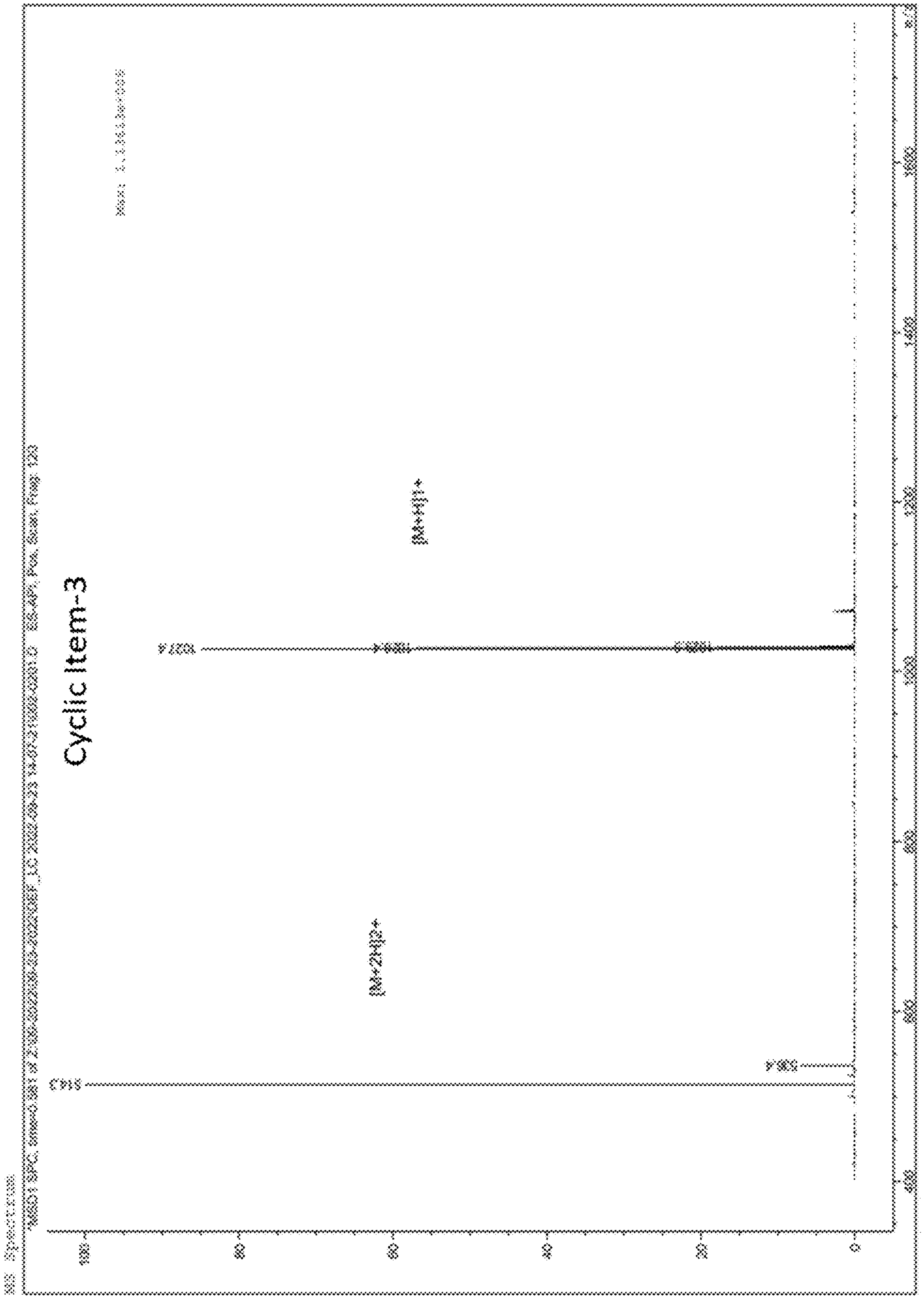
Figure 2B:
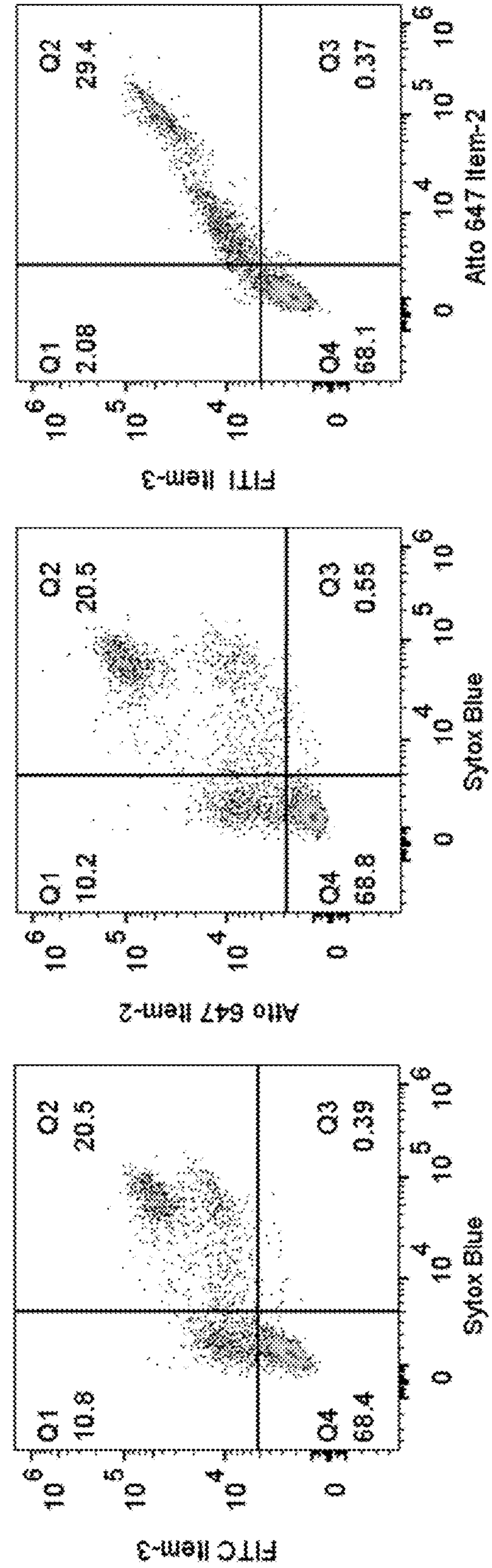
FIG. 2B shows the staining pattern and the frequency of PS positive cells simultaneously stained with FITC Item-3 and Atto 647 Item-2 on 2 days IL-4 stimulated U937 cells.

To validate FITC Item-3, the 2 days IL-4 stimulated cells were simultaneously stained with FITC Item-3 and Atto 647 Item-2 in PBS without $Ca^{2+}$. As shown in FIG. 2B, the staining pattern and the frequencies of PS positive dying cells and dead cells stained with FITC Item-3 and Atto 647 Item-2 are similar. Also, the PS positive cells stained with FITC Item-3 and Atto 647 Item-2 are highly related.

As described elsewhere herein, the experimental results illustrate that the PS binding compound derivative Item-3 has been successfully synthesized in present invention. Said Item-3 not only remains PS binding ability but also couples with azide-containing fluorophore for multicolor flow cytometry, which makes it possible to provide more options in selecting azide-containing different formats of fluorophores for multicolor flow cytometry and multiplex imaging. As the different azide-containing fluorophores are commercially available and conjugation method is well illustrated, the risk of manufacturing process and cost shall be reduced.

The PS binding compound derivative Item-3 couples with azide-containing Tag, wherein the azide-containing Tag may be an azide-containing amino acid including but not limited to azido-Lysine, azido-propargylglycine, azido-L-propargylglycine, azido-histidine, azido-tryptophan, azido-phenylalanine, azido-arginine, azido-glutamine, azido-glycine, azido-valine, azido-alanine, wherein azide group is used to link with alkyne group in Pra and amino acid having function group is used for chemical labelling.

The PS binding compound derivative Item-3 couples with azide-containing Tag, wherein the azide-containing Tag may also be an azide-containing bifunctional linker including but not limited to azide-Pol-maleimide, azide-Pol-thiol, azide-Pol-alkyne, azide-Pol-azide, azide-Pol-amine, azide-Pol-NHSter, and azide-Pol-COOH, wherein azide is used to link with alkyne in Pra of Item-3, wherein another functional group of amine, or NHSter, or carboxyl, or maleimide, or thiol, or alkyne, or azide in azide-containing bifunctional linker is used for chemical labelling; wherein Pol is a polymer used as a linker including but not limited to $(PEG)_n$, $(PEO)_n$, $(\varepsilon\text{-Caprolactam})_n$, $(CH2)_n$, and $[(PEG)_n(CH2)_n]$, wherein the n is the number of the polymers wherein n is an integer from 1 to 60, preferably 1 to 24, more preferably 1 to 12.

In present invention, the PS binding compound derivative Item-3 comprising the sequence of SEQ ID NO: 3 couples with azide-containing Tag, wherein said Tag is a detectable unit including but not limited to fluorophore, a solid phase carrier, an oligo, a biotin, an avidin, a protein, an enzyme, and a radionuclide. In addition, when said Tag is an azide-containing amino acid or an azide-containing bifunctional linker, wherein the said azide-containing amino acid or bifunctional linker may provide amine, or NHSter, or thiol, or maileimide, or azide, or alkyne and carboxyl group for chemical labelling.

The Item-2 and Item-3 in present invention can be labelled with maleimide or azide-containing fluorophore for imaging. The Arg and Lys in Item-2 or Item-3 cannot use for chemical labelling with NHSter-containing fluorophore because Arg and Lys are key elements for binding PS. Also, both Item-2 and Item-3 only have one functional group to bind one fluorophore. The ratio of fluorophore to Item-2 or Item-3 is 1:1 respectively. It is a challenge for the weak dyes for imaging, such as FITC. In order to create an amine group for amine-NHSter reaction and increase the fluorescence brightness, inventors designed a fusion of PS binding compound with an arm compound wherein the arm compound provides at least one amine functional group for chemical labelling.

The present invention provides for a fusion of PS binding compound with an arm compound comprising the sequence of SEQ ID NO: 5 [RKKWFWPra-Xa1(azido)-Xa2-(Pol-Xa3)$_m$] (Item-5), wherein an arm compound comprising the sequence of SEQ ID NO: 4 [Xa1(azido)-Xa2-(Pol-Xa3)$_m$] (Item-4) has been linked with Item-3 wherein the arm compound Item-4 provides at least one functional group to couple with at least one functional group containing Tag.

The method of making the fusion Item-5 and coupling with Tag comprises: (1) synthesizing Item-3 according to the sequence of SEQ ID NO: 3; (2) synthesizing arm compound Item-4 according to the sequence of SEQ ID NO: 4; (3) Linking Item 4 with Item-3 before coupling with maleimide or azide-containing Tag; (4) Item-4 coupling with NHSter-containing Tag before linking with Item-3.

The fusion Item-5 coupling with NHSter-containing fluorophore is used as an example for making and using Item-5, wherein NHSter-containing fluorophore couples with Item-4 by using amine-NHSter reaction before link with Item-3. The fluorophore is used as a detectable unit to be detected by flow cytometry for multicolor flow cytometry.

NHSter-containing fluorophore coupled with the fusion Item-5 was synthesized and validated by Mass Spectrometry and flow cytometry, wherein said variable amino acid [Xa1 (azido)] was Lys(azido); said variable amino acid (Xa2) was Lys, said variable (Pol-Xa3)$_m$ was (PEG4-Lys)$_3$; said PEG was Fmoc-NH-PEG-COOH, said Lys in (PEG4-Lys)$_3$ provided three amine groups to couple with three NHSter-containing fluorophores, wherein said fluorophore was NHSter-containing Fluorescein (FITC). The NHSter-containing Fluorescein (FITC) coupled with Item-5 was validated by flow cytometry.

Figure 3A:
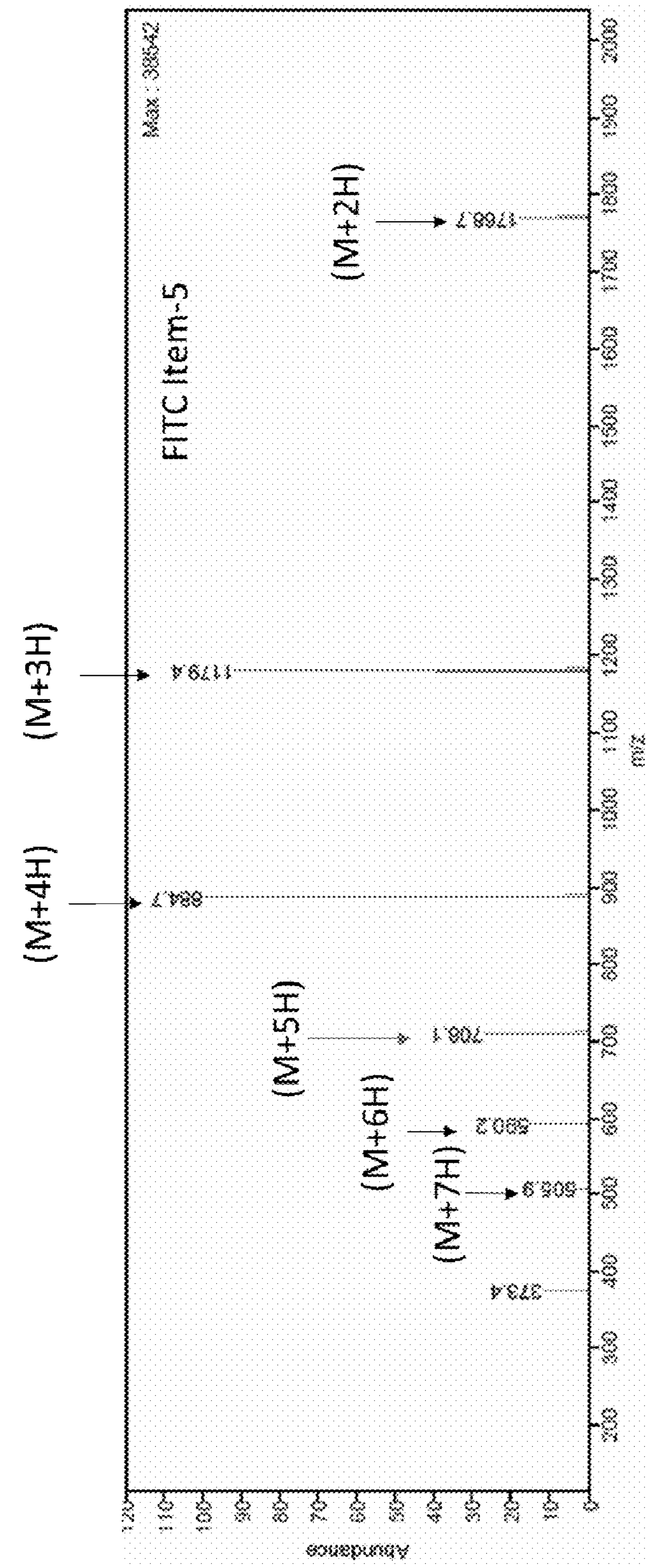
FIG. 3A shows the molecular weight of the fusion of PS binding compound with an arm comprising the sequence of SEQ ID NO: 5 (Item-5) coupled with FITC (FITC Item-5) measured by Mass Spectrometry.

As shown in FIG. 3A, the observed molecular weight of Item-5 is 3535.4 g/mole which indicates that Item-3 has linked with Item-4 and each Item-5 coupled with three FITCs.

Figure 3B:
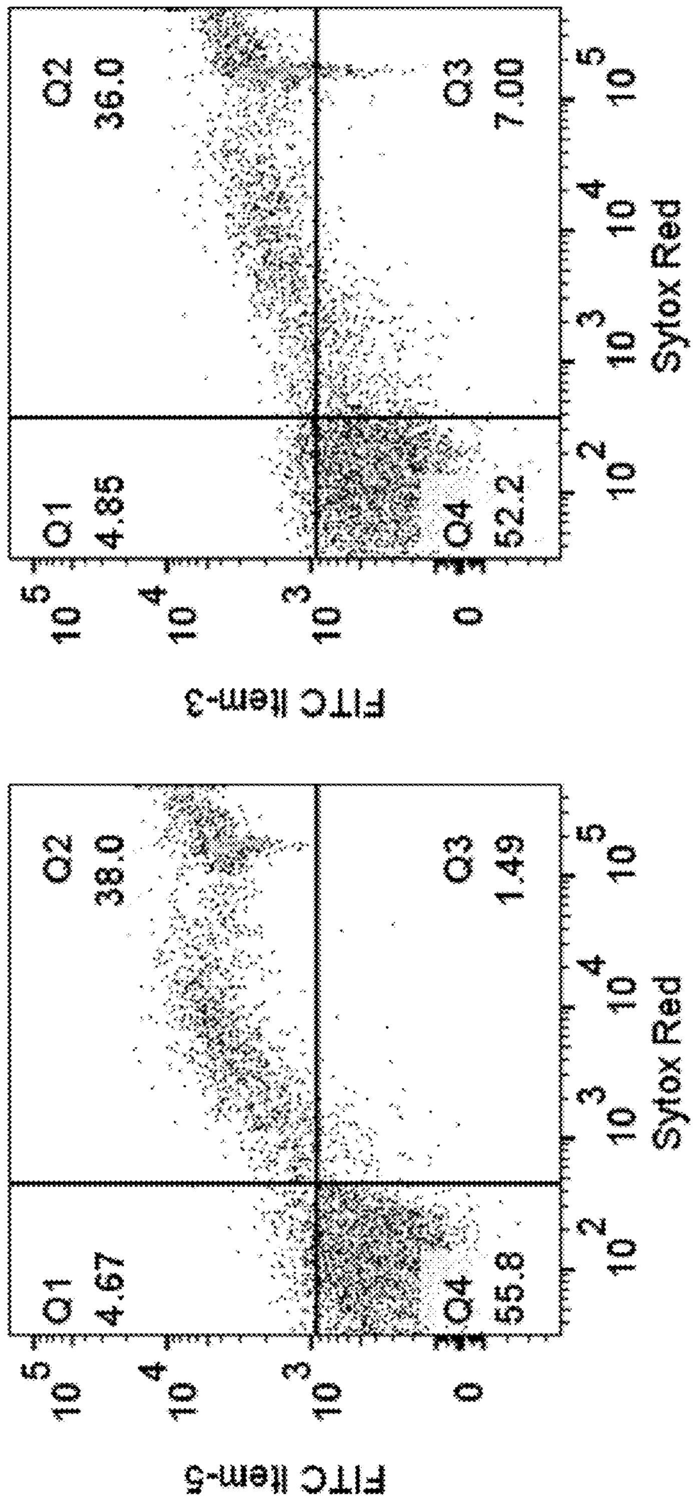
FIG. 3B shows the staining pattern and the frequency of PS positive cells stained with FITC Item-5 or FITC Item-3 on one day old C57BL/6 mouse thymocytes.

To validate the FITC Item-5, one day old C57BL/6 mouse thymocytes were side by side stained with FITC Item-5 or FITC Item-3 in PBS without $Ca^{2+}$. As shown in FIG. 3B, the staining pattern and the frequency of PS positive cells stained with FITC Item-5 and FITC Item-3 are comparable.

Figure 3C:
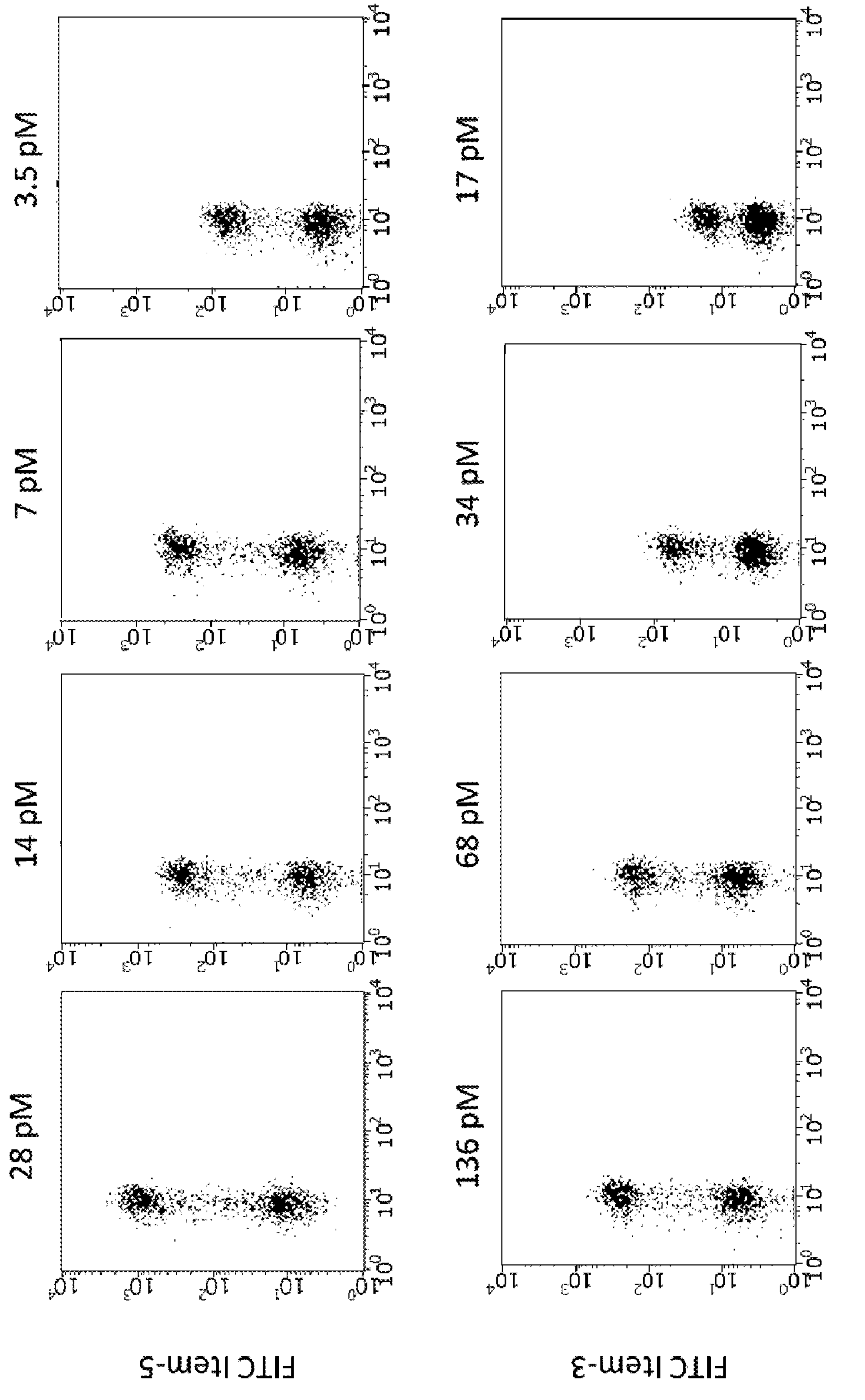
FIG. 3C shows the staining intensity of FITC Item-5 and FITC Item-3 in different concentrations on overgrew U937 cells.

Since the ratio of FITC to Item-5 is 3:1, FITC Item-5 staining fluorescence intensity should be stronger than FITC Item-3. As shown in FIG. 3C, the staining intensity of FITC Item-5 is higher than FITC Item-3 in different concentrations.

As described elsewhere herein, the experimental results illustrate that the FITC Item-5 has been successfully synthesized in present invention, which makes it possible to provide amine function group for coupling with NHSter-containing fluorophore by using amine-NHSter reaction. The Item-5 not only remains PS binding ability but also enables to couple with multiple fluorophores to enhance the fluorescence brightness for multicolor flow cytometry and multiplex imaging. Also, the number of amine functional groups can be modified by adding or reducing short repeated (PEG4-Lys).

The arm compound Item-4 comprising the sequence of SEQ ID NO: 4 wherein Xa1(azido) is an azide-containing amino acid including but not limited to azido-Lysine, azide-propargylglycine, azide-L-propargylglycine, azide-histidine, azide-tryptophan, azide-phenylalanine, azide-arginine, azide-glutamine, azide-glycine, azido-valine, and azido-alanine, wherein the azide group is used to link with alkyne in Pra of Item-3 and the amino acid having functional group is used to link with X2a.

The arm compound Item-4 comprising the sequence of SEQ ID NO: 4 wherein the variable Xa2 is an amino acid containing an amine group and a carboxyl group used as a liker to link with Xa1 and (Pol-Xa3) m, and wherein the amino acid includes but not limited to Lys, Arg, His, Ser, Thr, Cys, Asn, Gln, Pra, and Tyr.

The arm compound Item-4 comprising the sequence of SEQ ID NO: 4 wherein the $(Pol\text{-}Xa3)_m$ is an independent variable, wherein Pol is used as a linker including but not limited to $(PEG)_n$, $(PEO)_n$, $(\varepsilon\text{-Caprolactam})_n$, $(CH2)_n$, and $[(PEG)_n(CH2)_n]$, wherein the variable n is the number of polymers and n is an integer from 1 to 60, preferably 1 to 24, more preferably 1 to 12; said variable Xa3 is an amino acid having a functional group for chemistry labelling wherein the functional group includes but not limited to amine, thiol and alkyne, wherein the amino acid includes but not limited to Lys, Arg, His, Cys, and Pra; said variable m is the number of (Pol-Xa3), wherein m is an integer from 1 to 10.

In present invention, the fusion of PS binding compound with an arm comprising the sequence of SEQ ID NO:5 is able to provide amine, or thiol, or alkyne functional group to couple with NHSter, or maleimide, or azide-containing Tag, wherein Tag is used as a detectable unit including but not limited to fluorophore, oligo, solid phase carrier, biotin, avidin, protein, enzyme, radionuclide. In addition, the functional group provided by Item-5 can be selected for chemical coupling and the number of function groups provided by fusion Item-5 is adjustable.

The molecular weight of Item-2 and Item-3 is 1034.4 g/mol and 1026.4 g/mol respectively, which are smaller than protein dye, such as Phycoerythrin (PE) PE dye (molecular weight: 240,000 daltons). In order to label large size Tag such as PE or particle, inventors designed the second fusion of PS binding compound with an arm, wherein the arm provides a functional group for coupling a functional Tag.

The present invention provides for a fusion of PS binding compound with an arm compound comprising the sequence of SEQ ID NO: 7 [RKKWFWPra-Xa1(azido)-Xa2-Pol-Xa3] wherein an arm compound comprising the sequence of SEQ ID NO: 6 [Xa1(azido)-Xa2-Pol-Xa3] was linked with Item-3 wherein the arm compound Item-4 provides a functional group for coupling with a functional group containing Tag.

The method of making the Item-7 comprises: (1) synthesizing Item-3 comprising the sequence of SEQ ID NO: 3; (2) synthesizing Item-6 comprising the sequence of SEQ ID NO: 6; (3) linking Item-6 with Item-3 before coupling with the Tag containing maleimide or azide group; (3) Item-6 coupling with NHSter-containing Tag before link with Item-3.

The fusion Item-7 coupling with thiol-containing Tags are used as examples for making and using Item-7, wherein thiol-containing Tag couples with Item-7 by using thiol-maleimide reaction after linking Item-6 with Item-3.

The fusion Item-7 was synthesized and validated by Mass Spectrometry, wherein said variable Xa1 was Lys(azido), said variable Xa2 was Lys, said Pol was PEG12, said PEG was Fmoc-NH-PEG-COOH, said variable Xa3 was Cys to provide thiol group for coupling a maleimide-containing Tag.

Figure 4A:
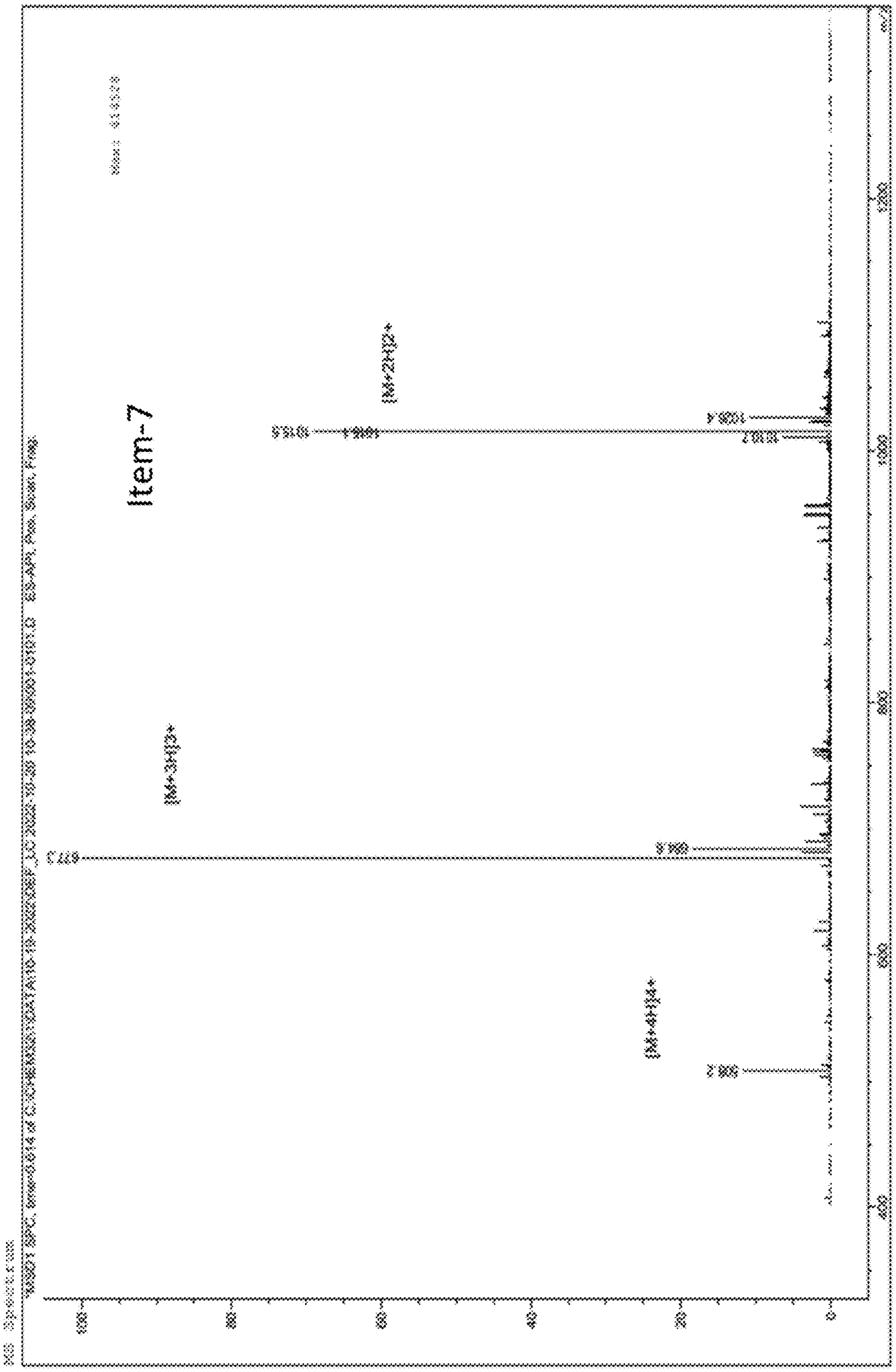
FIG. 4A shows the molecular weight of the fusion of PS binding compound with an arm comprising the sequence of SEQ ID NO: 7 (Item-7) measured by Mass Spectrometry.

As shown in FIG. 4A, the observed molecular weight of Item-7 is 2029 g/mole. The experimental results confirmed that Item-3 and Item-6 were successfully linked.

Figure 4B:
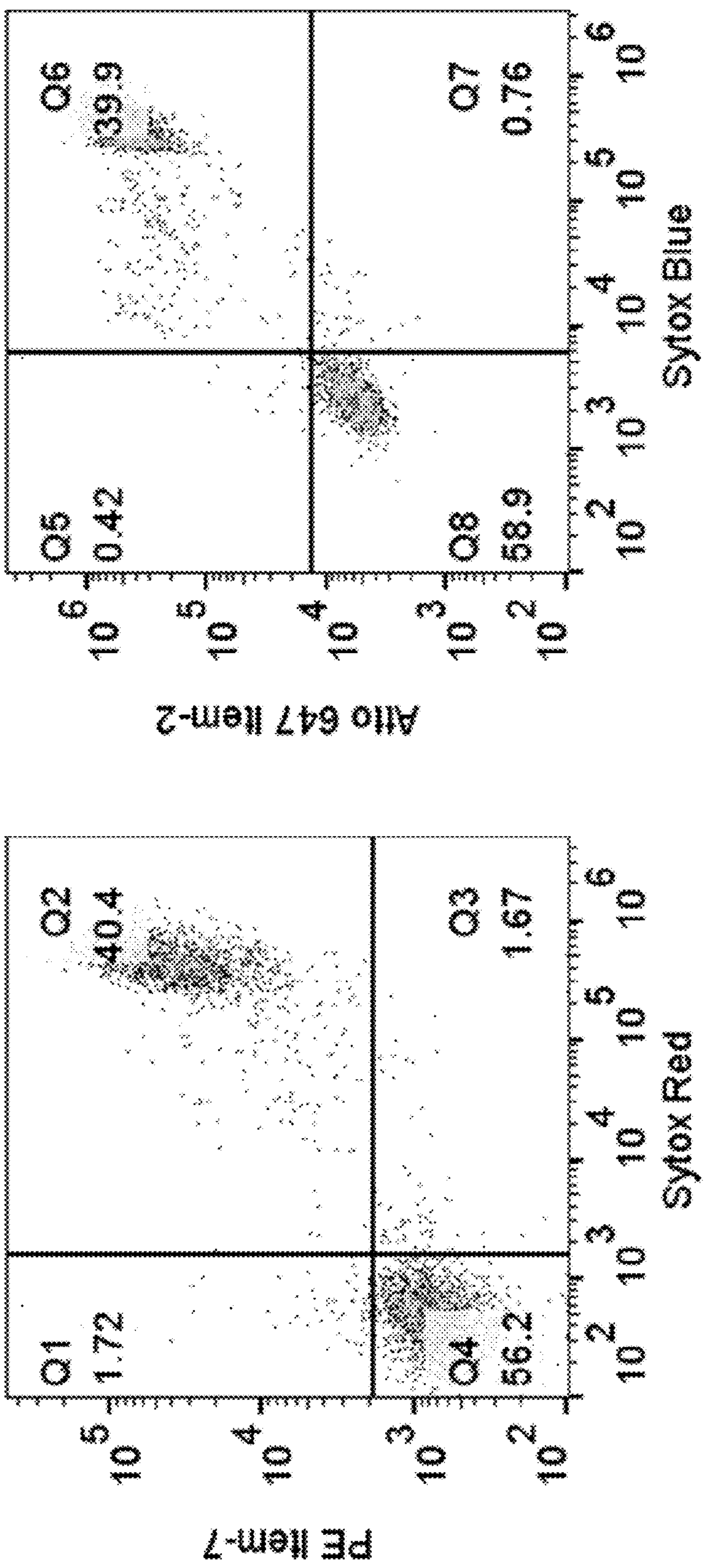
FIG. 4B shows the staining pattern and the frequency of PS positive cells stained with PE Item-7 or Atto 647 Item-2 on the mixture of fresh and heat shock treated Jurkat cells.

The maleimide-containing R-Phycoerythrin (PE) is used as an example for the method of making fluorophore labelled Item-7 and the method of using Item-7 for multicolor flow cytometry. The PE maleimide directly conjugated with Item-7 by using thiol-maleimide reaction and purified with S-200 column. As shown in FIG. 4B, the staining pattern and the frequency of PS positive cells stained with PE Item-7 or Atto 647 Item-2 are comparable in calcium independent manner. The experimental results show that the Item-7 can be used to couple with protein dye.

Figure 4C:
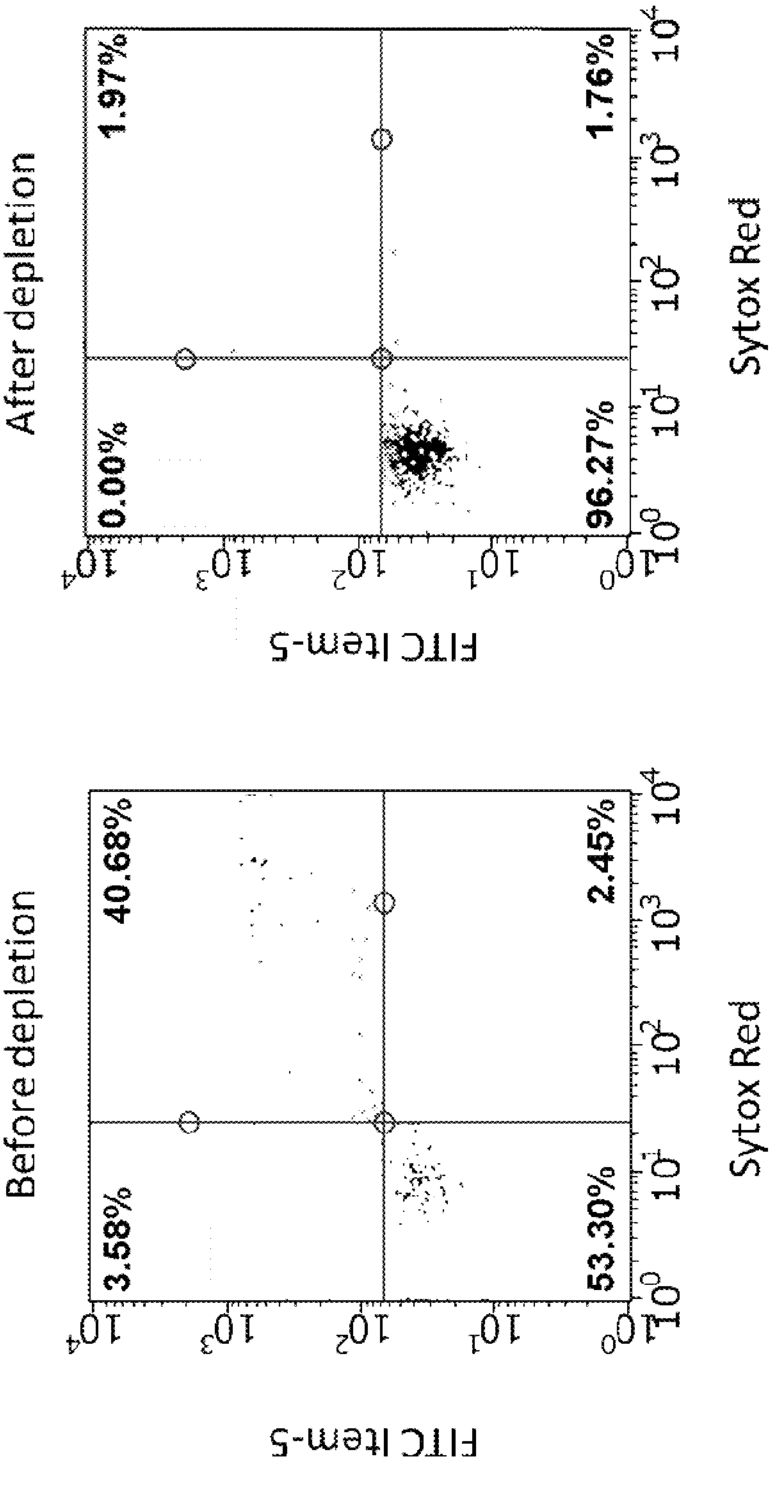
FIG. 4C shows the frequencies of PS positive and negative cells before and after depleting the PS positive cells from the mixture of fresh prepared and heat shock treated C57BL/6 mouse thymocytes.

The Item-7 conjugated magnetic particle is another example for the method of making magnetic particle conjugated Item-7 for depleting PS positive cells. As shown in FIG. 4C, Item-7 conjugated magnetic particles depleted PS positive cells with the mixture of fresh prepared and heat shock treated mouse thymocytes in cell separation buffer (buffer composition: PBS and 0.5% BSA and 2 mM EDTA) and the percentage of the live cells was increased from 53.3% to 96.27% by two separations and the recovery of live cells was 84%.

The Oligo labelled Item-7 is the yet another example for the method of making oligo coupled Item-7 for binding the PS positive cells in single-cell sequencing, wherein said oligo is a designed short DNA sequence comprising: (1) PCR handle sequence which serves as the starting point for DNA synthesis; (2) unique DNA barcode which serves as PS positive cell identifiers that can be easily recovered from single transcriptomes; (3) capture sequence which serves as a sequence to bind its complementary sequence on cell capture beads. Said oligo Item-7 is used to bind the PS positive cells which may discriminate PS positive cells from live in Single-cell RNA sequencing.

The experimental process Single-cell RNA sequencing includes: (1) oligo/DNA barcode labelled Item-7 contacts with the heterogeneous cellular population containing PS positive cells; (2) individual cell is captured in fluid flow device; (3) individual single cell is lysed; (4) individual cell is sequenced; (5) the sequence is analyzed.

The oligo labelled Item-7, wherein said oligo comprises the sequence of SEQ ID NO: 8, wherein said the sequence of SEQ ID NO: 9 is PCR handle which is a constant sequence identical on all primers to allow PCR amplification after single-cell transcriptomes attached to microparticles (STAMP) formation, and wherein said the sequence of SEQ ID NO: 10 is a unique cell barcode, which is the only identical sequence for PS positive cells which allows to recover the cells' origin. In the present invention, said unique cell barcode is used for identifying PS positive cells. Said the sequence of SEQ ID NO: 11 is 30-bp oligo-A capture sequence which serves as a sequence to bind its complementary sequence on cell capture beads co-encapsulate each cell individually with a distinctly barcoded microparticle in a tiny droplet. The "B" in said sequence represents either nucleotides C, or G, or T, and "*" indicates a phosphorothioated bond to prevent nuclease degradation. Once the individual cells are isolated in the individual droplets, the cells are lysed, which results in the mRNAs are released from the cells and hybridize to the primers, then generate STAMPs (single-cell transcriptomes attached to microparticles), then amplify the STAMPs followed by sequencing and analyzing by use of the STAMP barcodes to infer each transcript's cell of origin. The oligo can be designed with different sequences for different single cell sequence systems, including but not limited to 10× single cell sequencing system, Luminex single cell analysis system, BD Rhapsody single cell analysis system.

To validate if oligo Item-7 can specifically bind PS positive cells, Alexa 647 conjugated Poly-T has been made to hybridize with complementary sequence of poly-A. The 50 μM of oligo Item-7 was complementized with 37.5 μM of Alexa 647 conjugated Poly-T (Alexa 647 Poly-T oligo Item-7) at room temperature for 20 minutes first and then incubated with different heterogenous cellular populations for another 15 minutes followed by one wash. The cells stained with Atto 647 Item-2, or FITC Item-5 were used as control.

Figure 4D:
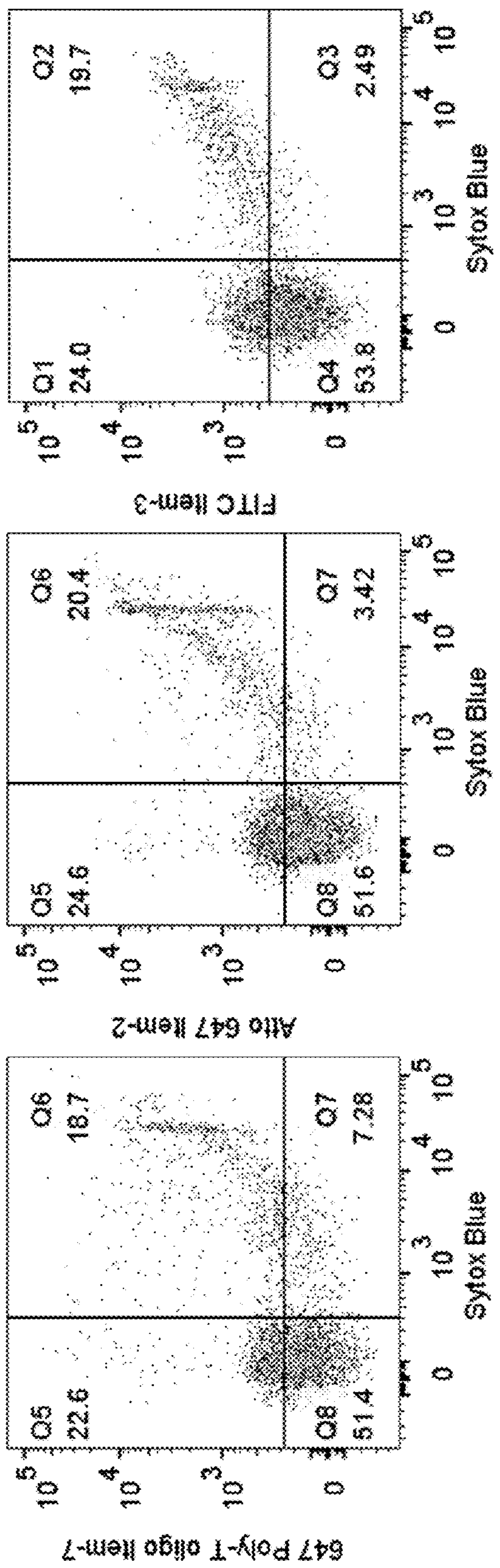
FIG. 4D shows the staining pattern and frequency of PS cells stained with pre-hybridized Alexa 647 Poly-T-oligo Item-7 (Alexa 647 Poly-T oligo Item-7), or Atto 647 Item-2 or FITC Item-5 on one day old C57BL/6 thymocytes.

FIG. 4D shows that the staining pattern and the frequency of PS positive cells stained with Alexa 647 Poly-T oligo Item-7, or Atto 647 Item-2, or FITC Item-5 are comparable on one day old mouse thymocytes.

Figure 4E:
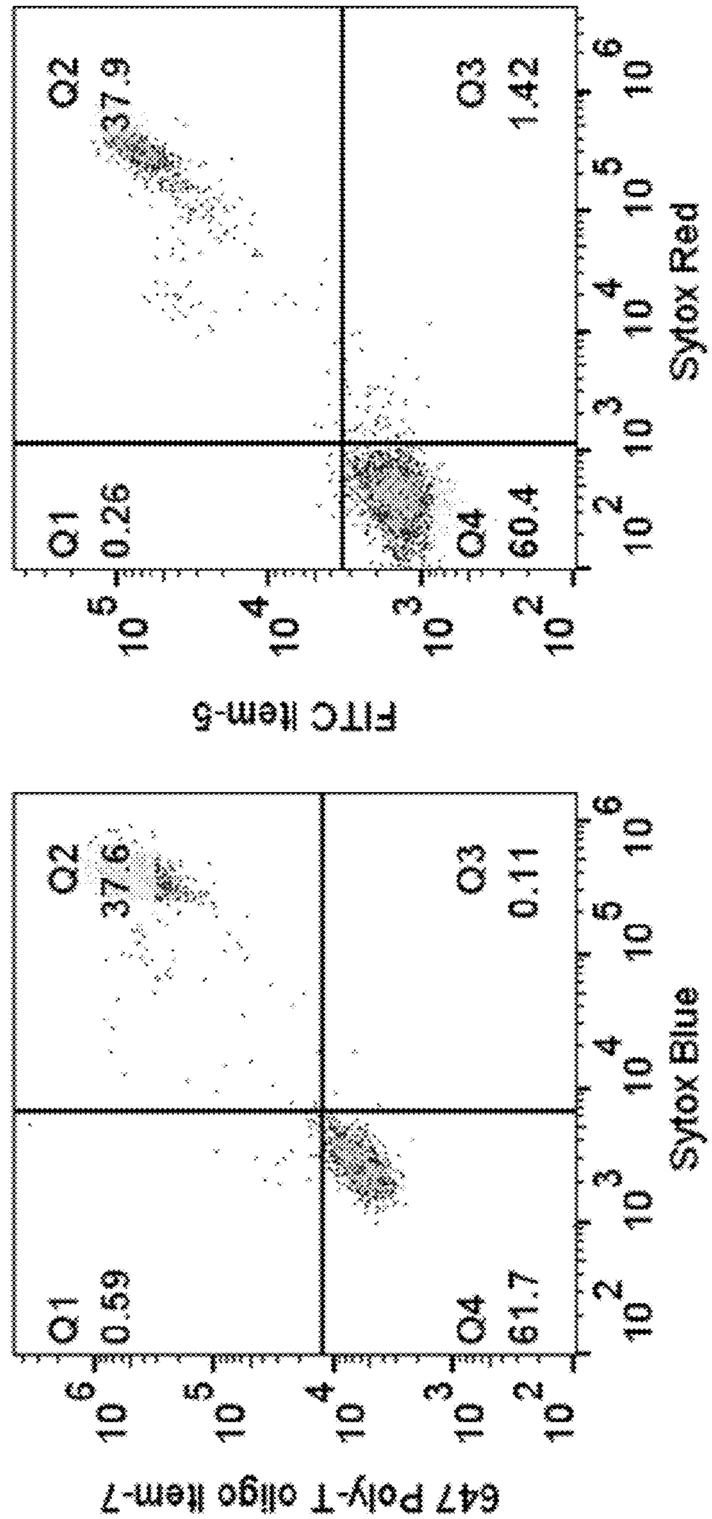
FIG. 4E shows the staining pattern and the frequency of PS positive cells stained with pre-hybridized Alexa 647 Poly-T-oligo Item-7 or FITC Item-5 on the mixture of live and heat shock treated Jurkat cells.

FIG. 4E shows that the staining pattern and the frequency of PS positive cells simultaneously stained with Alexa 647 Poly-T oligo Item-7 and Sytox Blue or FITC Item-5 and Sytox Red are similar on the mixture of live and heat shock treated Jurkat cells.

Figure 4F:
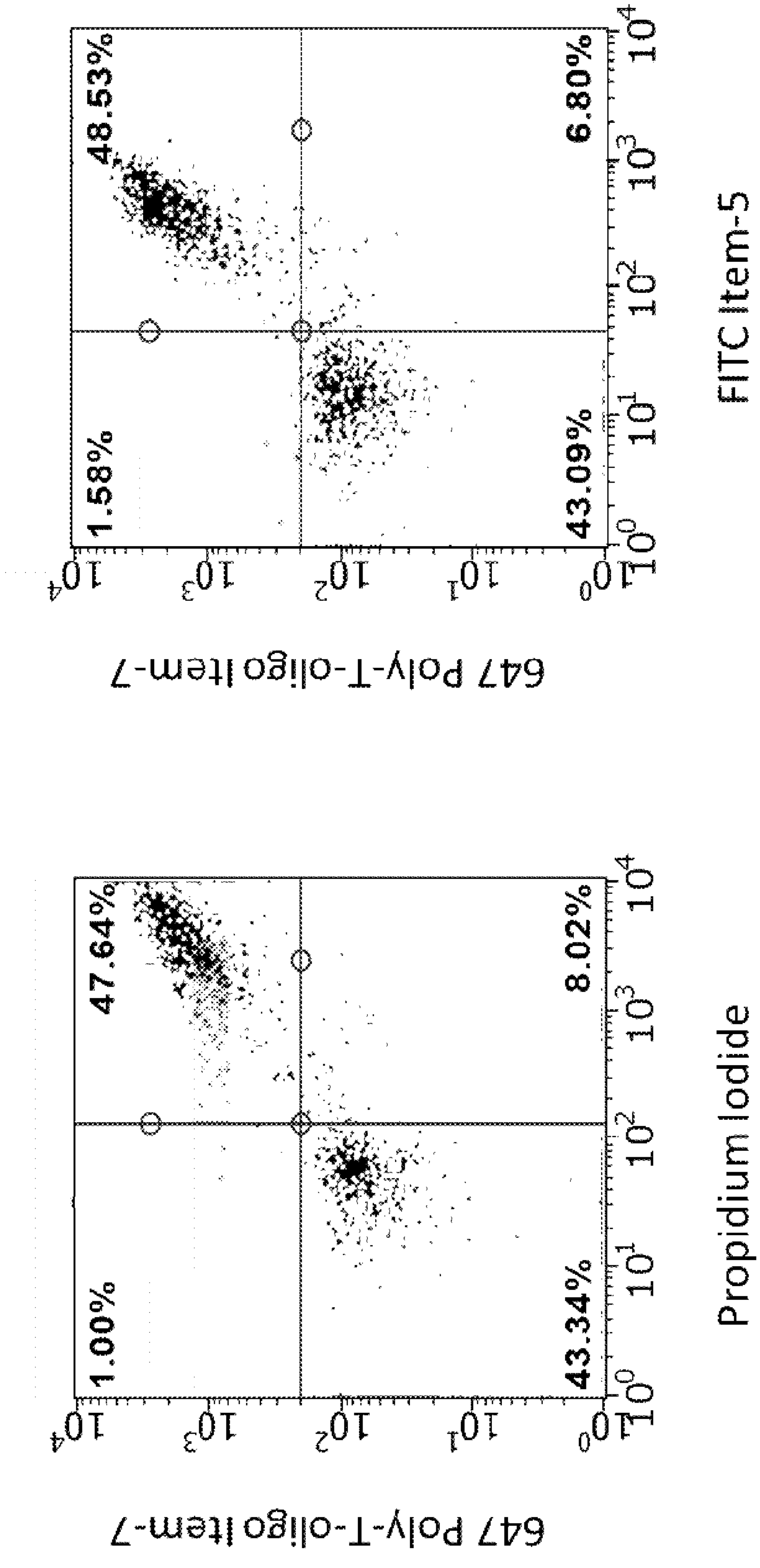
FIG. 4F shows the staining pattern and frequency of PS positive cells simultaneously stained with pre-hybridized Alexa 647 Poly-T oligo Item-7 and Propidium Iodide (PI) or FITC Item-5.

To further validate the specificity of oligo Item-7, the mixture of live and heat shock treated Jurkat cells were simultaneously stained with Alexa 647 Poly-T oligo Item-7 and Propidium Iodide (PI) or FITC Item-5. As shown in FIG. 4F, the PS positive cells simultaneously stained with 647 Poly-T oligo Item-7 are highly related to the PS positive cells stained with either Propidium Iodide or FITC Item-5.

As described elsewhere herein, the experimental results illustrate that the fusion Item-7 has been successfully synthesized in present invention. The fusion Item-7 not only remains PS binding ability but also enables to provide a thiol group with an adjustable linker which makes it possible to couple with maleimide-containing protein dye for multicolor flow cytometry, to couple with maleimide coated magnetic particles for depleting PS positive cells, to couple with maleimide contained oligo for binding the PS positive cells, which may discriminate PS positive cells from live cell in Single-cell RNA sequencing, wherein the oligo comprises PCR handing, and unique barcode for PS positive cells, and capture sequence.

Figure 4G:
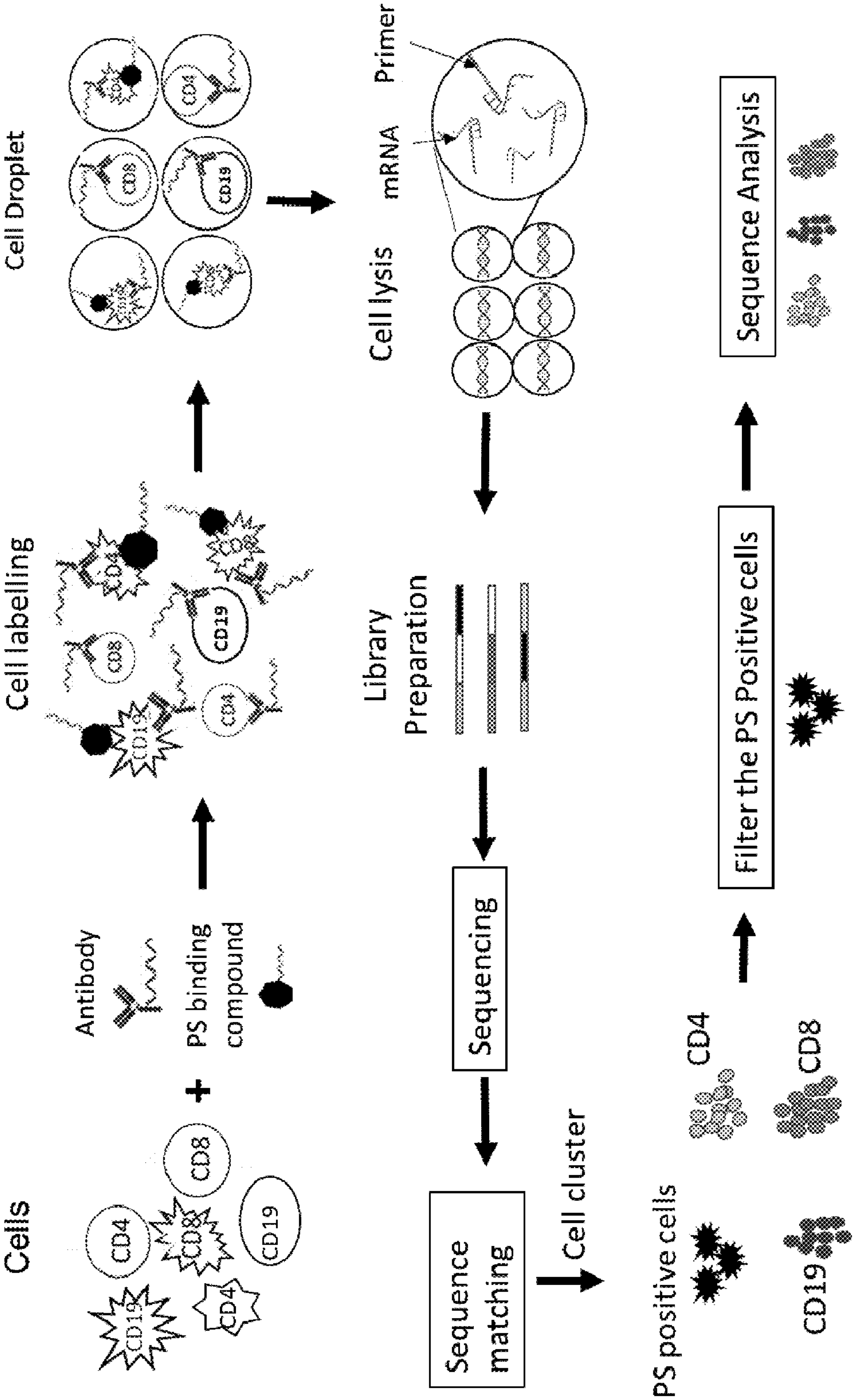
FIG. 4G illustrates a schematic diagram of the process for Single-cell sequencing.

FIG. 4G shows the schematic diagram of the process of single cell sequencing analysis. Oligo Item-7 is mixed with different oligo conjugated antibodies containing unique barcode to stain a heterogenous cellular population. The individual cells are captured in fluid flow device to co-encapsulate each cell individually with a distinctly barcoded microparticle in a tiny droplet by using Poly-A capture sequence to hybridize with complementary Poly-T beads. Once the cells are isolated in droplets, the cells are lysed, and mRNA is released, and hybridize to the primers. STAMPS is generated and then the STAMPS is amplified and sequenced. The bioinformatics scientist can perform the biological data analysis such as the sequence by using the STAMPS barcode to infer each transcript's cell of origin. Before the complex biological data analysis, PS positive cells are identified and filtered by unique barcode. Therefore, bioinformatics scientist will only analyze the live cells which effectively save time and improve the data quality.

The arm compound Item-6, wherein the variable said Xa1(azido) is an azide-containing amino acid including but not limited to azido-Lysine, or azido-propargylglycine, azido-L-propargylglycine, azido-histidine, azido-tryptophan, azido-phenylalanine, azido-arginine, azide-glutamine, azide-glycine, azido-valine, and azido-alanine, wherein azide group is used to link with alkyne group in Pra of Item-3 and amino acid having functional group is used to link with Xa2.

The arm compound Item-6, wherein the variable Xa2 is an amino acid containing an amine group and a carboxyl group used as a linker to link with Xa1 and Pol wherein an amino acid includes but not limited to Lys, Arg, His, Ser, Thr, Cys, Asn, Gin, Pra, and Tyr.

The arm compound Item-6, wherein Pol is used as a linker to link with Xa2 and Xa3, wherein Pol includes but not limited to $(PEG)_n$, $(PEO)_n$, $(\varepsilon\text{-Caprolactam})_n$, $(CH2)_n$, and $[(PEG)_n(CH2)_n]$, wherein the variable n is the number of polymers and n is an integer from 1 to 60, preferably 1 to 24, more preferably 1 to 12.

The arm compound Item-6, wherein the variable Xa3 is an amino acid used to provide a functional group for chemical labelling, wherein the variable Xa3 is a functional group containing amino acid, wherein the functional group includes but not limited to amine, thiol, and alkyne, and wherein the amino acid includes but not limited to Cys, Pra, Met, Lys, Arg, and His.

In present invention, the fusion of PS binding compound with an arm Item-7 comprising the sequence of SEQ ID NO:7 is able to provide amine, or thiol, or alkyne functional group to couple with NHSter, or maleimide, or azide-containing Tag, wherein Tag is used as a detectable unit including but not limited to fluorophore, oligo, solid phase carrier, biotin, avidin, protein, enzyme, radionuclide. In addition, the functional group provided by fusion Item-7 can be selected for chemical coupling. The length of the linker can be adjusted which may help to couple with large size Tag.

In present invention, the PS binding compound derivatives Item-2 and Item-3, and the fusions of PS binding compound with an arm compound Item-5 and Item-7 can couple with different functional groups containing Tag, wherein said Tag is used as a detectable unit. Said Tag is fluorophore used for multicolor flow cytometry and multiplex imaging, said Tag is solid phase carrier used for depleting PS positive cells, said Tag is oligo used for binding the PS positive cells, which may discriminate PS positive cells from live cells in Single-cell RNA sequencing, wherein the oligo comprises PCR handle sequence, unique DNA barcode for PS positive cells and capture sequence.

EXAMPLES

In order to better illustrate the claimed invention, the following examples are provided. The specific materials mentioned are merely for illustration purposes. There is no intent to limit the scope of the invention.

All chemicals obtained commercially were of analytical grade and used without further purification. All the amino acids were purchased form Sigma. Atto 647N maleimide was purchased from Sigma (Catalog number: 05316), Fluorescein Azide was purchased from Sigma (Catalog number: 910147), R-Phycoerythrin (PE) was purchased from Agilent (Catalog number: PB32B), Oligo was synthesized by Integrated DNA Technologies, Maleimide coated magnetic particles was purchased from Ocean NanoTech (Catalog number: SM0200-10).

Example 1

Synthesis and Validation of Item-2

The PS binding compound derivative Item-2 was synthesized by using standard Fmoc chemistry protocol according to the sequence of SEQ ID NO: 2. Then the crude peptide was purified by HPLC and the molecular weight was measured by Mass Spectrometry. The Atto 647N maleimide was coupled with Item-2 by using standard thiol-maleimide reaction chemistry protocol. The Atto 647N maleimide coupled Item-2 is named as Atto 647 Item-2 in present invention. Item-2 and Atto 647 Item-2 were synthesized and conjugated by Innopep Inc.

Figures 1, 1A, 2:
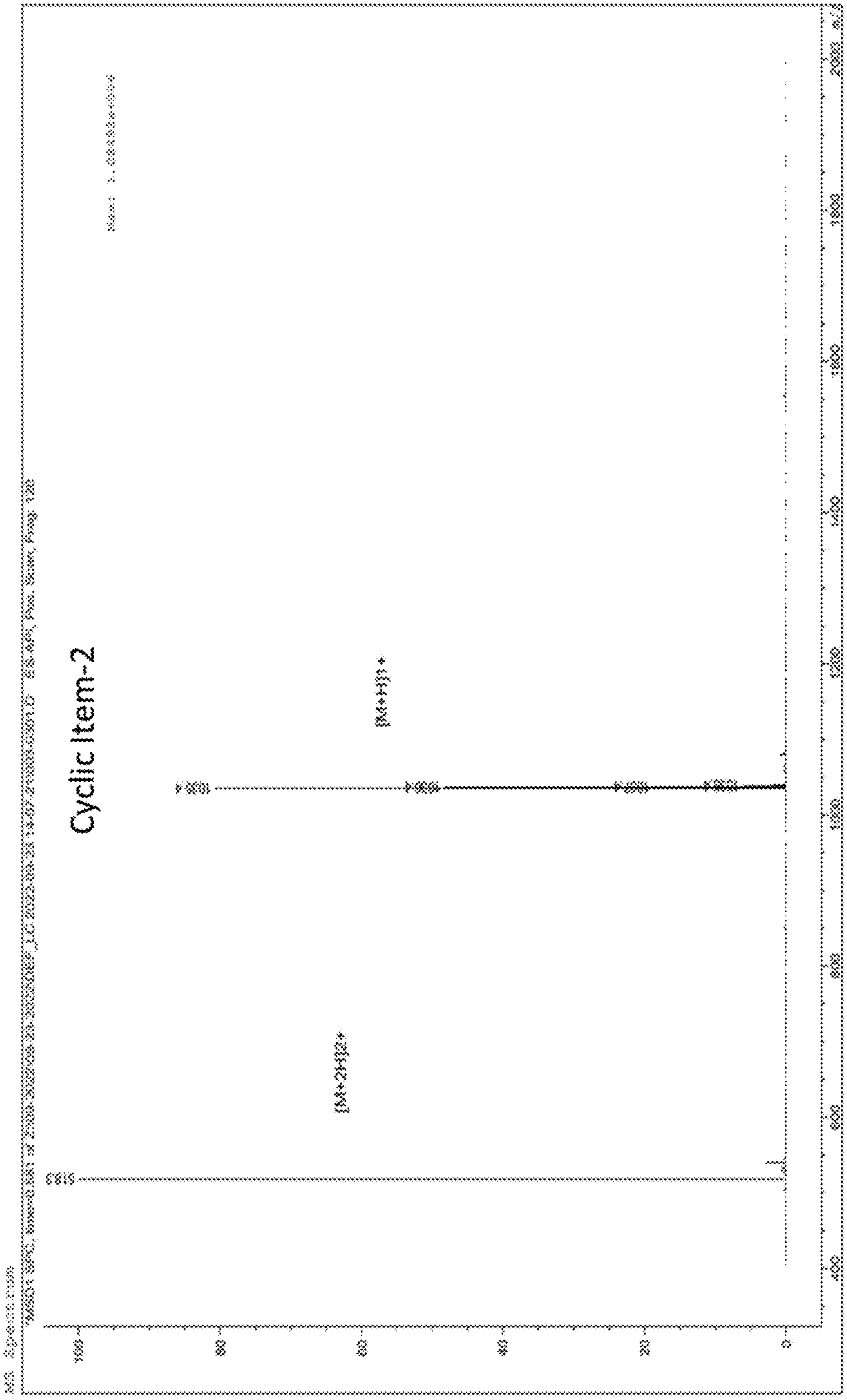
Figures 1, 1A, 2, 3:
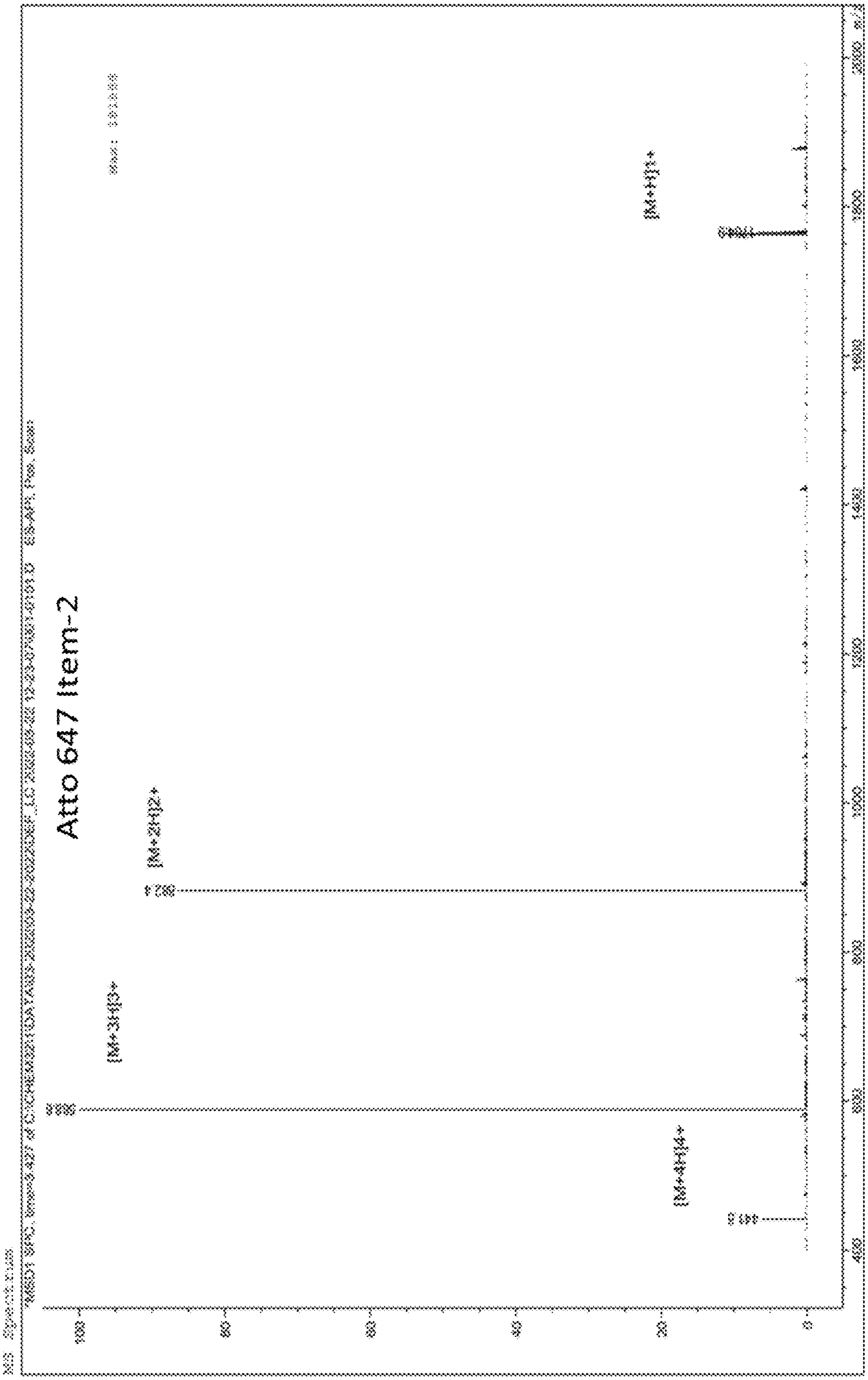
Figure 1B:
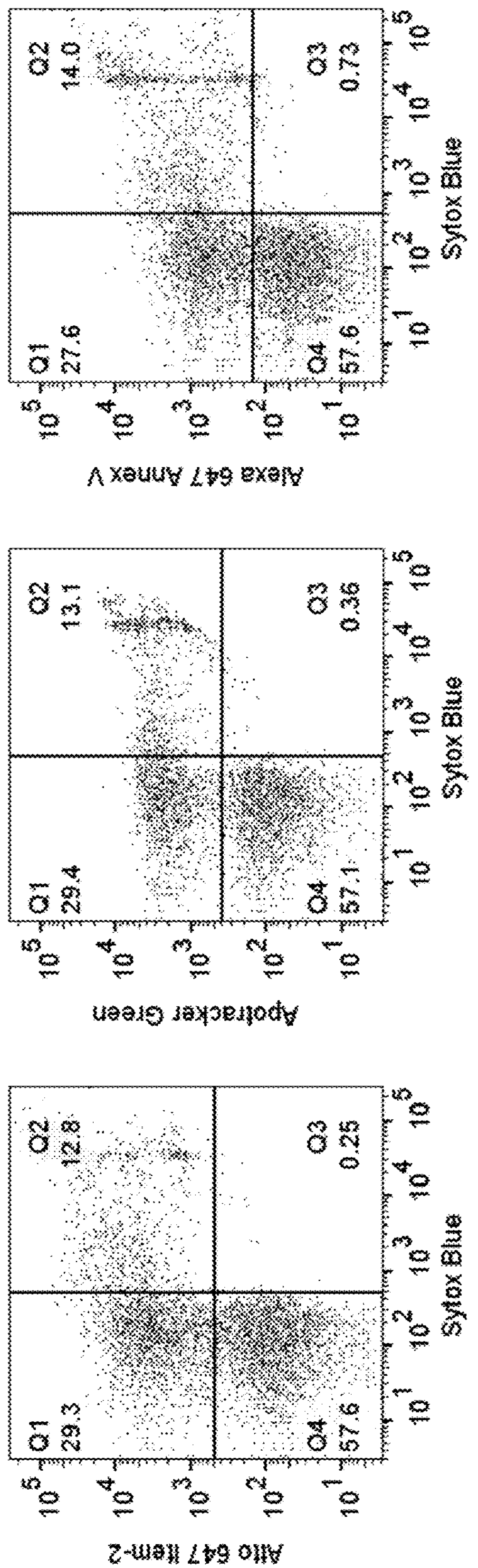
FIG. 1B shows the staining pattern and the frequency of PS positive cells stained with Atto 647 Item-2, or Apotracker Green or Alexa 647 Annexin V on one day old C57BL/6 mouse thymocytes.

FIG. 1A-1 through FIG. 1A-3 show the molecular weight of Item-2 measured by Mass Spectrometry. The molecular weight of linear Item-2 is 1052.4 g/mole as shown in FIG. 1A-1. During head-tail cyclization, carboxylic acid reacts with amine in the process of amidation. A water molecule is eliminated from the reaction and the amide is formed. The observed molecular weight of cyclic peptide of Item-2 is 1034.4 g/mole which subtracts $H_2O$ molecular weight from the molecular weight of linear Item-2 as shown in FIG. 1A-2. The Mass Spectrometry results confirmed that Item-2 was successfully synthesized and the purity of Item-2 is >95%. Also, Item-2 coupled with Atto 647 and the observed molecular weight of Atto 647 Item-2 is 1763.9 g/mole as shown in FIG. 1A-3. The purity of Atto 647 Item-2 is >95%.

To validate the Atto 647 Item-2 by flow cytometry, one day old C57BL/6 mouse thymocytes were side by side incubated with 28 μM/test of Atto 647 Item-2 and Sytox Blue or 400 nM/test of Apotracker and Sytox Blue in PBS without $Ca^{2+}$ or 5 μL/test of Alexa 647 Annexin V and of Sytox Blue in Annexin V binding buffer for 15 minutes at room temperature, then the cells were analyzed with NovoCyte Quanteon flow cytometry without wash. Debris were gated out based on cell density plot in a lower level of forward scatter. The two-parameter density plots show Atto 647 Item-2 or Apotracker Green or Annexin V versus Sytox Blue. Sytox Blue is an impermeant blue-emitting nucleic acid indicator which is used for indicating the dead cells. Sytox Blue was used at 20 nM/test in herein.

As shown in FIG. 1B, the Atto 647 Item-2-Sytox cells are live cells shown in Q4, the Atto 647 Item-$2^+$ Sytox are dying cells shown in Q1 and the Item-$2^+$ $Sytox^+$ are dead cells shown in Q2. The frequencies of PS positive cells stained with Atto 647, or Apotracker Green in PBS without $Ca^{2+}$, or Annexin V in Annexin V binding buffer are comparable to each other on one day old C57BL/6 mouse thymocytes. The cells were analyzed with NovoCyte Quanteon flow cytometry without wash.

Figure 1C:
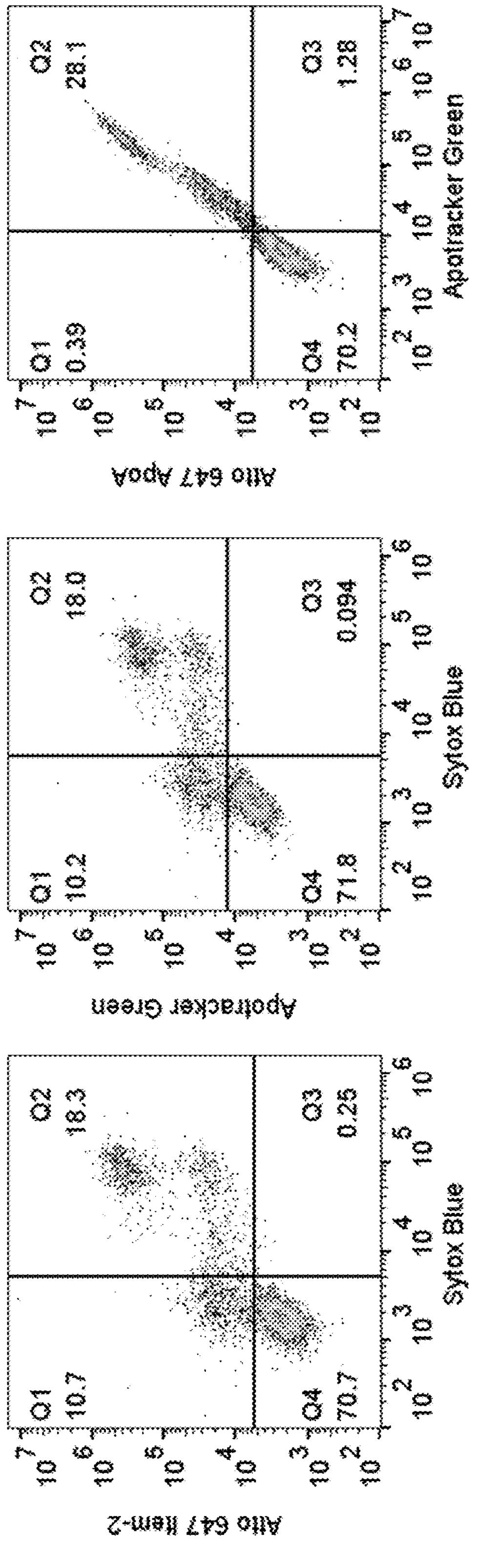
FIG. 1C shows the staining pattern and the frequency of PS positive cells simultaneously stained with Atto 647 Item-2, and Apotracker Green on 2 days IL-4 stimulated U937 cells.
Figure 1D:
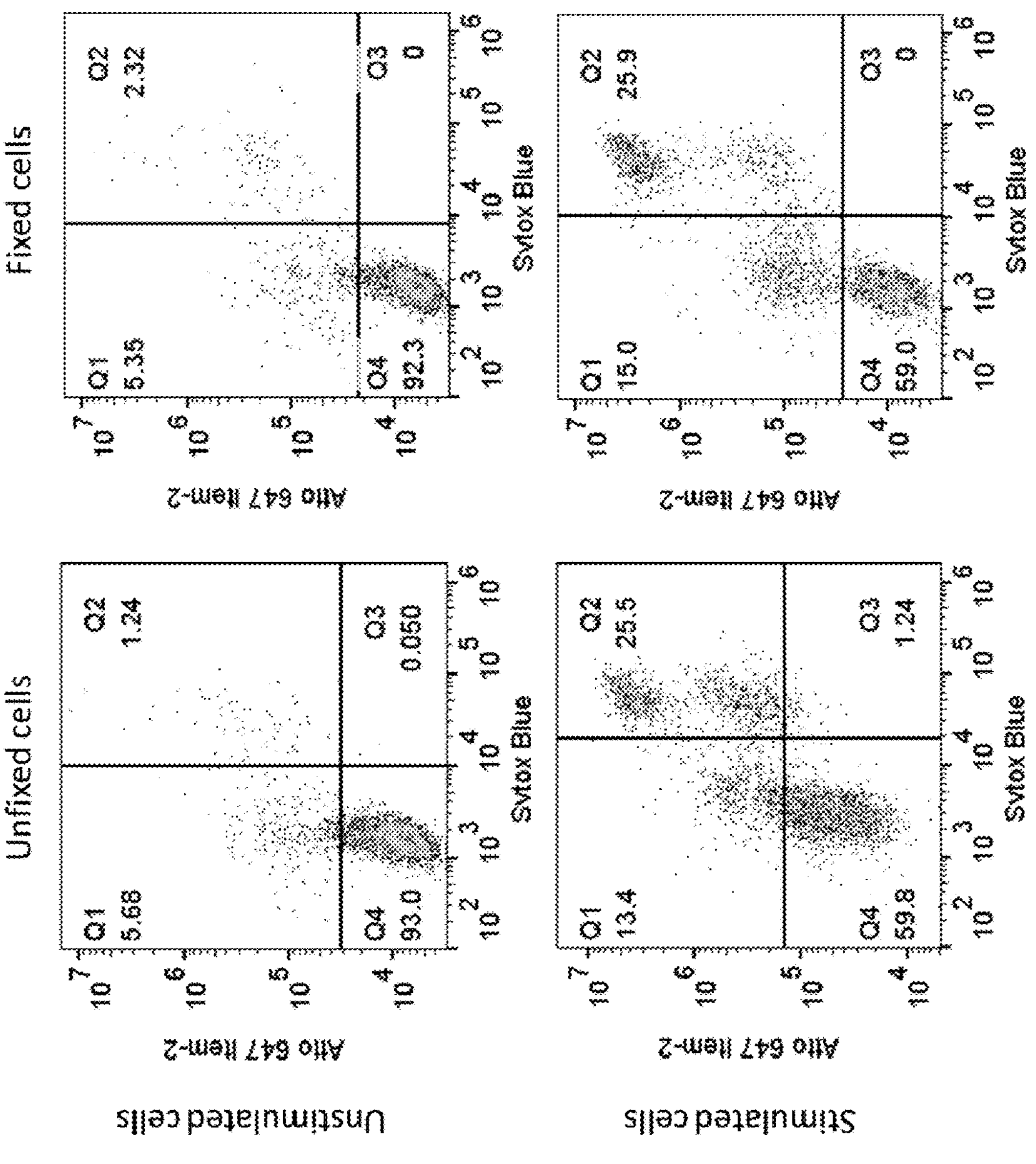
FIG. 1D shows staining pattern and the frequency of PS positive cells stained with Atto 647 Item-2 with fresh and 2 days IL-4 stimulated U937 cells before and after fixation.
Figure 1E:
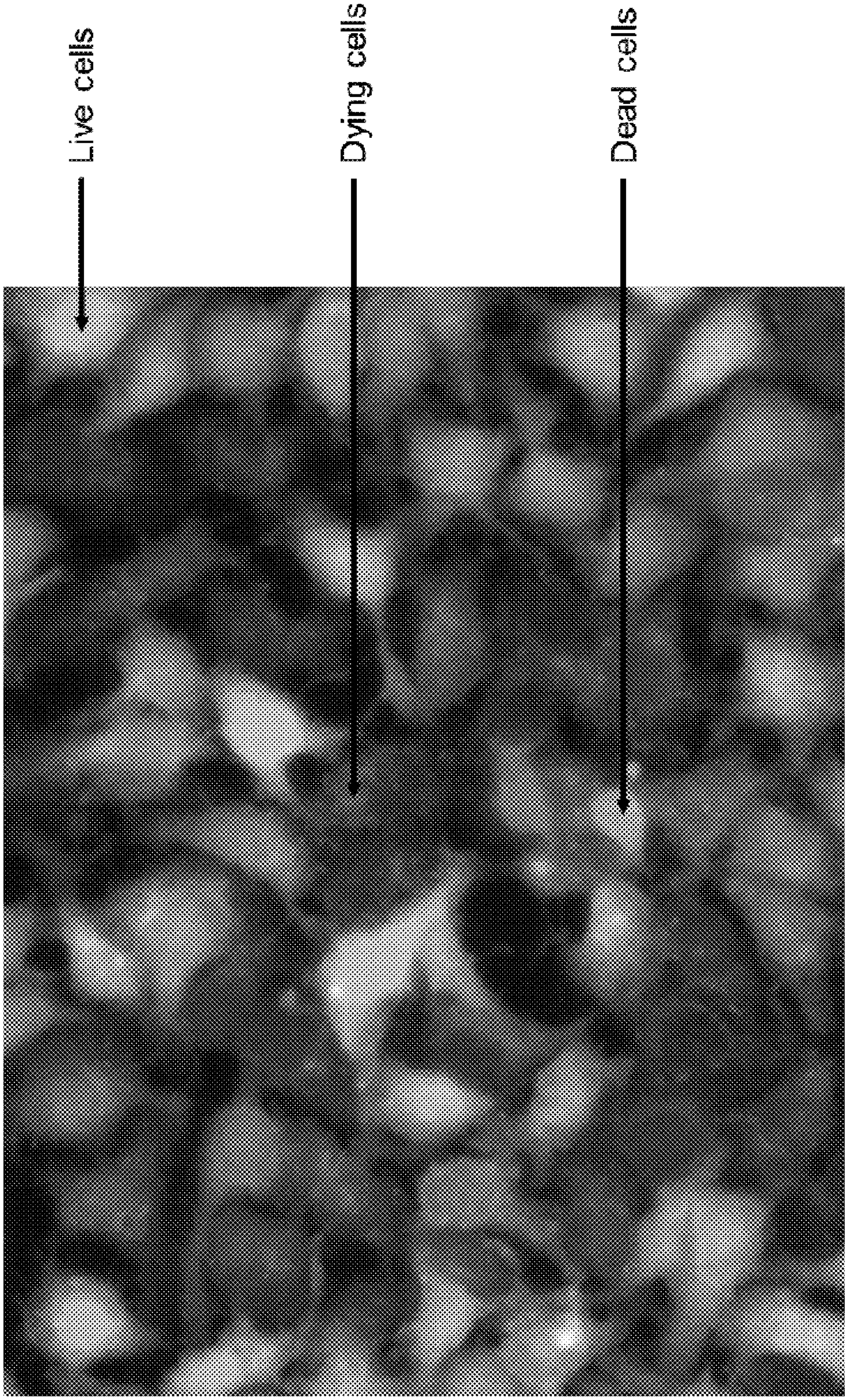
FIG. 1E shows multiplex image simultaneously stained with Calcein AM, Atto 647 Item-2, and Fixable viability dye-405.

To validate the relationship of the PS positive cells stained with Atto 647 Item-2 and Apotracker Green, 2 days IL-4 stimulated U937 cells were simultaneously stained with 28 μM/test of Atto 647, and 400 nM of Apotracker Green and 50 nM of Sytox Blue in original cell culture medium for 5 minutes and then the cells were analyzed with NovoCyte Quanteon flow cytometry without wash. As shown in FIG. 1C, the staining patten and the frequencies of the live cells, PS positive dying cells and dead cells stained with Atto 647 Item-2 and Apotracker Green are similar. In two-parameter density plots of Atto 647 Item-2 vs Apotracker Green, PS positive dying cells and dead cells show diagonal distribution.

To further study the relationship between the PS positive dying cells and dead cells stained with Atto 647 Item-2 and Apotracker Green, the correlation coefficient is used. Table 1 shows the frequencies of live cells and PS positive dying cells and dead cells from four independent experiments with different types of cells in different concentrations of Atto 647 Item-2 and Apotracker Green in PBS without $Ca^{2+}$. The cells were analyzed with NovoCyte Quanteon flow cytometry without wash.

The correlation evaluates the strength of the relationship between the PS positive dying cells and dead cells stained with Atto 647 Item-2 and Apotracker Green.

TABLE 1

| | | Concentration | | | | | | | | |
|---|---|---|---|---|---|---|---|---|---|---|
| | Atto 647 Item-2 | 7 pM | | | 14 pM | | | 28 pM | | |
| | Apotracker Green | 100 nM | | | 200 nM | | | 400 nM | | |
| | | Dying cells Q1 (%) | Dead cells Q2 (%) | Live cells Q4 (%) | Dying cells Q1 (%) | Dead cells Q2 (%) | Live cells Q4 (%) | Dying cells Q1 (%) | Dead cells Q2 (%) | Live cells Q4 (%) |
| Exp 1 | Atto 647 Item-2 | 2.5 | 27.1 | 68.4 | 2.22 | 29.5 | 66.1 | 3.31 | 28.5 | 66.8 |
| | Apotracker Green | 2.97 | 28.3 | 67.7 | 2.86 | 30.3 | 66.1 | 2.89 | 29.5 | 67.2 |
| Exp 2 | Atto 647 Item-2 | 10.4 | 23.81 | 64.62 | 11.91 | 23.18 | 64.42 | 10.7 | 18.3 | 70.7 |
| | Apotracker Green | 11.73 | 23.4 | 64.76 | 11.41 | 23.4 | 64.76 | 10.2 | 18.0 | 71.8 |
| Exp 3 | Atto 647 Item-2 | 0.68 | 35.35 | 58.08 | 1.06 | 32.92 | 62.05 | 2.6 | 31.33 | 64.24 |
| | Apotracker Green | 1.15 | 34.58 | 59.91 | 0.05 | 32.3 | 61.77 | 3.41 | 26.12 | 64.8 |
| Exp 4 | Atto 647 Item-2 | 2.68 | 8.4 | 84.46 | 2.58 | 9.36 | 86.93 | 4.5 | 8.5 | 84.96 |
| | Apotracker Green | 2.4 | 10.03 | 82.76 | 5.65 | 9.83 | 84.12 | 4.92 | 9.72 | 83.62 |

The correlation can be computed using the following formula:

$$\rho(X, Y) = \frac{\mathrm{Cov}(X, Y)}{\sigma_X \sigma_Y}$$

Where:

$\rho(X,Y)$—the correlation between the variables X and Y $\mathrm{Cov}(X,Y)$—the covariance between the variables X and Y $\sigma_x$—the standard deviation of the X-variable.

$\sigma_y$—the standard deviation of the Y-variable

Covariance between two variables can be calculated as follows:

$$\mathrm{Cov}(X, Y) = \frac{\sum (X_i - X_{avg})(Y_j - Y_{avg})}{n-1}$$

Where:

$X_i$—the values of the X-variable $Y_j$—the values of the Y-variable $X_{avg}$—the mean (average) of the X-variable.

$Y_{avg}$—the mean (average) of the Y-variable n—the number of data points

Base on the experimental results shown in Table 1, the correlation between the live cells, PS positive dying cells and dead cells stained by Atto 647 Item-2 and Apotracker Green was computed as shown in Table 2:

TABLE 2

| | Correlation Coefficients between Atto 647 Item-2 and Apotracker Green |
|---|---|
| Dying cells | 0.963 |
| Dead cells | 0.984 |
| Live cells | 0.998 |

The correlation coefficients are very close to 1.0, which means that the live cells, the PS positive dying cells and dead cells stained by Atto 647 Item-2 and Apotracker Green show very strong positive correlation and have an almost perfect linear relationship. Both experimental and calculated results verified that the PS positive dying cells and dead cells stained with Atto 647 Item-2 and Apotracker Green are highly related.

In order to validate if the PS positive cells stained with Atto 647 Item-2 are fixable, the fresh and 2 days IL-4 stimulated U937 cells were simultaneously stained with 28 μM/test of Atto 647 Item-2 and 20 nM of Sytox Blue, then the cells were split into two sets. One set of cells were analyzed with flow cytometry right after staining without wash, the other set of cells were fixed by adding 16% of Paraformaldehyde (PFA) to the final concentration at 2% PFA for 10 minutes at room temperature followed by centrifugation at 350 g for 5 minutes. Then the cells were resuspended in PBS without $Ca^{2+}$. The fresh cells and stimulated cells with or without fixation were analyzed on day 0 and day 2 respectively. The cells were analyzed with NovoCyte Quanteon flow cytometry without wash.

As shown in FIG. 1D, the staining pattern and the frequency of PS positive cells are similar before and after fixation in both stimulated and unstimulated samples. Since there was a wash step after fixation, the fluorescence intensity on fixed cells is slight lower than unfixed cells. The experimental results confirmed that Item-2 binding PS positive cells is $Ca^{2+}$ independent and the PS positive cells stained with Item-2 are fixable.

To further validate if the PS cells stained with Atto 647 Item-2 are visualized by fluorescence microscope, the adherent human lung adenocarcinoma cell line (CaLu-06) cells were exposure to the UV light for 20 minutes and then simultaneously stained with Calcein AM 1 μg/100 μL and Atto 647 Item-2 at 84 μM/100 μL and Fixable viability dye 405 at 1 μL/100 μL at room temperature for 15 minutes in PBS without $Ca^{2+}$ followed by one wash. Then the cells were imaged with Leica DMi8 microscopy. Calcein AM is membrane-permeable live-cell labeling dye which labels live cells. Fixable viability dye 405 reacts with protein amine groups in compromised cell membrane which labels dead cells. The image was captured with individual filter and all the individual image were overlayed with LAS X software.

As shown in FIG. 1E, Calcein $AM^+$ Atto 647 Item-2-Fixable viability dye 405-cells are live cells, Calcein $AM^{weak/-}$ Atto 647 Item-$2^+$ positive and Fixable viability dye 405-cells are dying cells, Calcein AM-Atto 647 Item-$2^+$ Fixable viability dye 405+ cells are dead cells. The experimental results show that Atto 647 Item-2 can be used for multiplex imaging.

Example 2

Synthesis and Validation of Item-3

PS binding compound derivative Item-3 was synthesized by using standard Fmoc chemistry protocol according to the sequence of SEQ ID NO: 3. Then the crude peptide was purified by HPLC and the molecular weight was measured by Mass Spectrometry. The FITC Item-3 was conjugated by using standard azide-alkyne reaction chemistry protocol. Item-3 was synthesized by Innopep Inc.

FIG. 2A-1 and FIG. 2A-2 show the molecular weight of Item-3 measured by Mass Spectrometry. The molecular weight of linear Item-3 is 1044.5 g/mole as shown in FIG. 2A-1. The observed molecular weight of cyclic Item-3 is 1026.5 g/mole because one $H_2O$ molecular weight is eliminated during head-tail cyclization (see FIG. 2A-2). The experimental results confirmed that Item-3 was successfully synthesized. The purity of Item-3 is >95%.

To characterize FITC Item-3, 2 days IL-4 stimulated U937 cells were simultaneously stained with 68 μM/test of FITC Item-3 and 28 pM/test of Atto 647 Item-2 and 20 nM of Sytox Blue in PBS without $Ca^{2+}$ buffer for 5 minutes and then the cells were analyzed with NovoCyte Quanteon flow cytometry without wash.

As shown in FIG. 2B, the staining pattern and the frequency of PS positive dying cells and dead cells stained with FITC Item-3 and Atto 647 Item-2 are similar. In addition, PS positive dying cells and dead cells stained with FITC Item-3 and Atto 647 Item-2 are highly related.

Example 3

Synthesis and Validation of FITC Item-5

The fusion of PS binding compound with an arm compound Item-5 coupled with FITC was synthesized comprising: (1) Item-3 was synthesized by using standard Fmoc chemistry protocol according to the sequence of SEQ ID NO: 3; (2) arm compound Item-4 was synthesized by using standard Fmoc chemistry according to the sequence of SEQ ID NO: 4; (3) NHSter-containing FITC was coupled with Item-4 by using standard amine-NHSter reaction chemistry protocol; (4) Item-3 was then linked with FITC coupled Item-4 by using standard azide-alkyne reaction chemistry protocol. Then the crude peptide was purified by HPLC and the molecular weight was measured by Mass Spectrometry. FITC Item-5 was synthesized by WuXi AppTec.

FIG. 3A shows the molecular weight of FITC Item-5 measured by Mass Spectrometry. As shown in FIG. 3A, the observed molecular weight of Item-5 is 3535.4 g/mole. Item-4 was linked with Item-3 and each Item-5 coupled with three FITCs. The experimental results confirmed that FITC Item-5 was successfully synthesized. The purify is 94.7%.

To characterize the FITC Item-5, one days old mouse thymocytes were simultaneously stained with 5 nM of Sytox Red and 14 μM of FITC Item-5 or 68 pM of FITC Item-3 in PBS without $Ca^{2+}$ for 5 minutes without wash. Then the cells were analyzed by NovoCyte Quanteon flow cytometry. Based on the data shown in FIG. 3A, one Item-5 is coupled with three FITC, the FITC Item-5 staining intensity should be stronger than FITC Item-3. To further compare the staining intensity between FITC Item-5 and FITC Item-3, the overgrowth U937 cells were side-by-side stained with different concentrations of FITC Item-5 and FITC Item-3 for 5 minutes without wash. The cells were analyzed with Guava® EasyCyte™ Flow Cytometer (Luminex Corporation).

As shown in FIG. 3B, the staining pattern and the frequency of PS cell stained by FITC Item-5 and FITC Item-3 are similar on one day old C57BL/6 mouse thymocytes.

As shown in FIG. 3C, the fluorescence staining intensity of FITC Item-5 is higher than FITC Item-3 at different concentrations on overgrowth U937 cells. The optimal concentration for FITC Item-5 and FITC Item-3 is at 14 pM and 68 pM respectively. The cells were analyzed with Guava® EasyCyte™ Flow Cytometer (Luminex Corporation).

Example 4

Synthesis and Validation of Item-7

The fusion of PS binding compound with an arm compound Item-7 was synthesized comprising: (1) Item-3 was synthesized by using standard Fmoc chemistry protocol according to the sequence of SEQ ID NO: 3; (2) Item-6 was synthesized by using standard Fmoc chemistry protocol according to the sequence of SEQ ID NO:6; (3) Item-6 was linked with Item-3 by using standard azide-alkyne reaction chemistry protocol. The crude peptide was purified by HPLC and the molecular weight was measured by Mass Spectrometry. Item-7 was synthesized by Innopep Inc.

As shown in FIG. 4A, the observed molecular weight of Item-7 is 2029 g/mole. The experimental results confirmed that the Item-3 and Item-6 were successfully linked. The purity of Item-7 is >94%.

Phycoerythrin (PE) maleimide was conjugated with Item-7 by using the standard protocol for thiol-maleimide reaction and PE Item-7 was purified by sizing through S-200 column. To characterize PE Item-7, the mixture of live and heat shock treated Jurkat cells were side by side stained with 2.4 μg/100 μL PE Item-7 and 5 nM of Sytox Red or 28 μM/test of Atto 647 Item-2 and 20 nM of Sytox Blue in original cell culture medium for 15 minutes with one wash. Then the cells were analyzed by NovoCyte Quanteon flow cytometry.

As shown in FIG. 4B, the staining pattern and the frequency of PS cells stained with PE Item-7 and Atto 647 Item-2 are similar on the mixture of live and heat shock treated Jurkat cells.

To validate if Item-7 can be conjugated with solid phase carrier for depleting PS positive cells, maleimide coated magnetic particles were conjugated with Item-7 by using standard thiol-maleimide chemistry protocol. The Item-7 conjugated magnetic particles were washed and sonicated to remove aggregated particles. Then the mixture of fresh prepared and heat shock treated C57BL/6 mouse thymocytes were suspended in cell separation buffer (buffer composition: PBS and 0.5% FCS and 2 mM EDTA) at $1\times10^7$/mL. Then $1\lambda10^6$/100 μL of cells were transferred into a FACS tube and incubated with 10 μL of Item-7 conjugated magnetic particles at room temperature for 15 minutes. The cells were then diluted with cell separation buffer up to 3 mL and placed in the separator for 5 minutes. Then the suspended cells were poured into a new collecting tube. To further increased the live cell purity, the cells in the collecting tube were placed in the separator for another 5 minutes and the suspended cells were poured into another new collecting tube. After two separations, the cells without separation and the cells in the collecting tube after separation were centrifugated and then resuspended in 100 μL of PBS without $Ca^{2+}$. The resuspended cells were then stained with 14 μM FITC Item-5 and 5 nM of Sytox Red at room temperature for 5 minutes without wash. The cells were analyzed by Guava® EasyCyte™ Flow Cytometer (Luminex Corporation).

As shown in FIG. 4C, Item-7 conjugated magnetic particles depleted the PS positive cells and increased the percentage of the live cells from 53.3% to 96.27%. The yield of live cells is 84%.

The Maleimide-containing oligo comprising the sequence of SEQ ID NO:8 contains PCR handle sequence of SEQ ID NO: 9, unique DNA barcode sequence of SEQ ID NO: 10, and capture sequence of SEQ ID NO: 11 (Poly-A). Oligo Item-7 was conjugated by using standard thiol-maleimide chemistry protocol and purified by S-200 column. To validate if oligo Item-7 can specifically bind PS positive cells, Alexa 647 conjugated Poly-T has been made, which can hybridize with complementary sequence of SEQ ID NO: 11 (Poly-A). The 50 μM of oligo Item-7 was complementized with 37.5 μM of Alexa 647 conjugated Poly-T at room temperature for 20 minutes first and then incubated with different heterogenous cellular populations for another 15 minutes followed by one wash. The cells stained with 28 μM/test of Atto 647 Item-2, or 14 μm/test of FITC Item-5 were used as control. Sytox Blue at 20 nM was used to stain the PS positive dead cells. Then the cells were analyzed with NovoCyte Quanteon Flow Cytometer.

As shown in FIG. 4D, the staining pattern and the frequency of PS positive cells stained with Alexa 647 Poly-T oligo Item-7 are similar to the PS positive cells stained with Atto 647 Item-2 and FITC Item-5 on one day old C57BL/6 mouse thymocytes.

The mixture of live and heat shock treated Jurkat cells were stained with 50 μM of pre-hybridized Alexa 647 Poly-T oligo Item-7 and 20 nM of Sytox Blue or 14 μM of FITC-Item-5 and 5 nM of Sytox Red in original cell culture medium for 15 minutes and the cells were then analyzed with NovoCyte Quanteon Flow Cytometer without wash. The staining pattern and the frequency of PS positive cells stained with 647 Poly-T oligo Item-7 and FITC Item-5 are also comparable (see FIG. 4E).

The mixture of live and heat shock treated Jurkat cells were simultaneously staining with 50 μM of pre-hybridized Alexa 647 Poly T-oligo Item-7 and Propidium Iodide at 2 μL/100 μL or 14 μM of FITC Item-5 in original cell culture medium for 15 minutes. Then the cells were analyzed with Guava® EasyCyte™ Flow Cytometer (Luminex Corporation). As shown in FIG. 4F, the PS positive cells simultaneously stained with Alexa 647 Poly T-oligo Item-7 and Propidium Iodide are highly related. And the PS positive cells simultaneously stained with Alexa 647 Poly-T oligo Item-7 and FITC Item-5 are also highly related. This experiment has been repeated for 3 times. The data from FIG. 4D, FIG. 4E and FIG. 4F demonstrate that oligo Item-7 can bind PS positive cells.

FIG. 4G shows the flow chart of single cell sequencing. Oligo labelled Item-7 is mixed with different oligo conjugated antibodies containing unique barcodes and the cocktail is incubated with a heterogenous cellular population followed by one wash. Then the individual cells are captured in microfluidic devices to co-encapsulate each cell individually with a distinctly barcoded microparticle in a tiny droplet by using Poly-A capture sequence to hybridize with complementary Poly-T beads. Once the cells are isolated in droplets, the cells are lysed, and mRNA is released and hybridized to the primers. STAMPS is generated and the STAMPS is amplified and sequenced. The bioinformatics scientist can then perform the biological data analysis such as the RNA sequence by using the STAMPS barcode to infer each transcript's cell of origin. Before the complex biological data analysis, PS positive dying cells and dead cells are identified by unique barcode and filtered by using pattern/sequence matching tool. In this way, bioinformatics scientist will only analyze the live cells which will effectively save the time and improve the data quality.

The invention claimed is:

1. A fusion compound comprising:

a phosphatidylserine (PS) binding compound comprising a cyclic peptide comprising the amino acid sequence RKKWFWPra (SEQ ID NO: 3), wherein the first amino acid and the seventh amino acid are connected to form the cyclic peptide;

a compound comprising an amine functional group, a thiol functional group, or an alkyne functional group; and an oligonucleotide.

2. The fusion compound of claim 1, wherein the compound comprising an amine functional group, a thiol functional group, or an alkyne functional group comprises Lys (azido)-Lys-PEG12-Cys.

3. The fusion compound of claim 2, wherein the fusion compound comprises the structure: RKKWFWPra-Lys (azido)-Lys-PEG12-Cys-oligonucleotide.

4. The fusion compound of claim 3, wherein Pra is conjugated to Lys through an azide-alkyne chemical reaction.

5. The fusion compound of claim 1, wherein the oligonucleotide comprises a PCR handle sequence, a unique DNA barcode sequence, and a capture sequence.

6. The fusion compound of claim 5, wherein the PCR handle sequence comprises the nucleotide sequence CCTTGGCACCCGAGAATTCCA (SEQ ID NO: 9).

7. The fusion compound of claim 5, wherein the unique DNA barcode sequence comprises the nucleotide sequence ATCGTCGAGAGCTAG (SEQ ID NO: 10).

8. The fusion compound of claim 5, wherein the capture sequence comprises the nucleotide sequence AAAAAAAAAAAAAAAAAAAAAAAAAAAA*A*A (SEQ ID NO: 11), wherein the asterisk * indicates the two adjoining nucleotides are connected by a phosphorothioate bond.

9. The fusion compound of claim 1, wherein the oligonucleotide comprises the nucleotide sequence CCTTGGCACCCGAGAATTCCAATCGTCGAGAGC-TAGBAAAAAAAAAAAAAAAAAAA AAAAAAAAA*A*A (SEQ ID NO: 8), wherein the asterisk * indicates the two adjoining nucleotides are connected by a phosphorothioate bond.

10. The fusion compound of claim 1, wherein the fusion compound comprises the structure: RKKWFWPra-Lys (azido)-Lys-PEG12-Cys-CCTTGGCACCCGAGAATTC-CAATCGTCGAGAGCTAGBAAAAAAAAAAAAA-AAAAAAA AAAAAAAA*A*A, wherein the asterisk * indicates the two adjoining nucleotides are connected by a phosphorothioate bond.

11. The fusion compound of claim 1, wherein the oligonucleotide comprises a PCR handle sequence that serves as a starting point for DNA synthesis in a PCR amplification.

12. The fusion compound of claim 11, wherein the PCR handle sequence comprises the nucleotide sequence CCTTGGCACCCGAGAATTCCA (SEQ ID NO: 9).

13. The fusion compound of claim 1, wherein the oligonucleotide comprises a unique DNA barcode sequence.

14. The fusion compound of claim 13, wherein the unique DNA barcode sequence comprises the nucleotide sequence ATCGTCGAGAGCTAG (SEQ ID NO: 10).

15. The fusion compound of claim 1, wherein the oligonucleotide comprises a capture sequence.

16. The fusion compound of claim 15, wherein the capture sequence comprises the nucleotide sequence AAAAAAAAAAAAAAAAAAAAAAAAAAAA*A*A (SEQ ID NO: 11), wherein the asterisk * indicates the two adjoining nucleotides are connected by a phosphorothioate bond.

17. The fusion compound of claim 1, wherein the oligonucleotide comprises a sequence that serves as a starting point for DNA synthesis in a PCR amplification, a sequence that serves as a phosphatidylserine (PS) positive cell identifier, and a sequence for binding a complementary sequence for capture.

* * * * *